US011160836B2

(12) United States Patent
Gianello et al.

(10) Patent No.: US 11,160,836 B2
(45) Date of Patent: Nov. 2, 2021

(54) TRANSGENIC PIG ISLETS AND USES THEREOF FOR TREATING DIABETES

(71) Applicant: UNIVERSITÉ CATHOLIQUE DE LOUVAIN, Louvain la Neuve (BE)

(72) Inventors: Pierre Gianello, Rixensart (BE); Nizar Mourad, Brussels (BE)

(73) Assignee: UNIVERSITÉ CATHOLIQUE DE LOUVAIN, Louvain la Neuve (BE)

( * ) Notice: Subject to any disclaimer, the term of this patent is extended or adjusted under 35 U.S.C. 154(b) by 0 days.

(21) Appl. No.: 15/303,447

(22) PCT Filed: Apr. 10, 2015

(86) PCT No.: PCT/EP2015/057914
§ 371 (c)(1),
(2) Date: Oct. 11, 2016

(87) PCT Pub. No.: WO2015/155360
PCT Pub. Date: Oct. 15, 2015

(65) Prior Publication Data
US 2017/0189453 A1    Jul. 6, 2017

(30) Foreign Application Priority Data

Apr. 11, 2014 (EP) .................................. 14164372
Dec. 22, 2014 (EP) .................................. 14199910

(51) Int. Cl.
| | |
|---|---|
| *A61K 35/39* | (2015.01) |
| *A61K 35/12* | (2015.01) |
| *A01K 67/027* | (2006.01) |
| *A61K 9/06* | (2006.01) |
| *A61K 38/26* | (2006.01) |
| *C07K 14/605* | (2006.01) |
| *C12N 5/071* | (2010.01) |
| *C12N 15/85* | (2006.01) |

(52) U.S. Cl.
CPC .......... *A61K 35/39* (2013.01); *A01K 67/0275* (2013.01); *A61K 9/06* (2013.01); *A61K 38/26* (2013.01); *C07K 14/605* (2013.01); *C12N 5/0677* (2013.01); *C12N 15/8509* (2013.01); *A01K 2207/12* (2013.01); *A01K 2217/072* (2013.01); *A01K 2227/108* (2013.01); *A01K 2267/00* (2013.01); *A61K 2035/128* (2013.01); *C12N 2015/8536* (2013.01)

(58) Field of Classification Search
None
See application file for complete search history.

(56) References Cited

U.S. PATENT DOCUMENTS

| | | | |
|---|---|---|---|
| 6,191,102 B1* | 2/2001 | DiMarchi | A61K 38/26 514/11.7 |
| 9,458,214 B2* | 10/2016 | Boettcher | C07K 14/50 |
| 2008/0032317 A1* | 2/2008 | Pausch | C07K 14/705 435/7.31 |
| 2014/0017678 A1* | 1/2014 | Cesano | C12N 15/1137 435/6.11 |

FOREIGN PATENT DOCUMENTS

| | | |
|---|---|---|
| JP | 2013501528 | 1/2013 |
| WO | 2002032437 | 4/2002 |
| WO | 2002060409 | 8/2002 |
| WO | 2006110054 | 10/2006 |
| WO | 2007046719 | 4/2007 |
| WO | 2007144389 | 12/2007 |
| WO | 2010/032242 | 3/2010 |
| WO | 2011020120 | 8/2010 |
| WO | 2012113859 | 8/2012 |

OTHER PUBLICATIONS

Seffernick et al., J. Bacteriol., 2001, 183: 2405-2410.*
Witkowski et al., Biochemistry, 1999, 38: 11643-11650.*
Chae et al., Transplantation International, 2011, 25: 242-249.*
Buteau, Diabetes & Metabolism, 2008, 34: S73-S77.*
Jay et al., Xenotransplantation, 1999, 6: 131-140.*
Komatsu et al., Proc. Natl. Acad. Sci. USA, 1995, 92: 10728-10732.*
Sequence alingment, 2018.*
Chae et al., Transplant International, online Jan. 24, 2013, 26: 443-452.*
Gautam et al., Endocrinology, 2010, 151: 5185-5194.*
Yu et al., Diabetes, 2000, 49: 945-952.*
Niwa, Pancreas, 2001, 22: 135-140.*
Bertuzzi et al. "Intercellular Ca2+ waves sustain coordinate insulin secretion in pig islets of Langerhans" FEBES Letters, 1996, 379:21-25.
Crowther et al. "Porcine islet isolation, cellular composition and secretory response" Horm. Metabol. Res, 1989, 21:590-595.
Dufrane & Gianello, "Pig islet xenotransplantation into non-human primate model" Transplantation, 2008, 86(6), 753:60.
Dufrane et al. "Nutrient control of insulin secretioni in perifused adult pig islets" Diabetes & Metabolism, 2007, 33:430-438.
Dufrane et al., "Alginate Macroencapsulation of Pig Islets Allows Correction of Streptozotocin-Induced Diabetes in Primates up to 6 Months Without Immunosuppression" Transplantation, 2010, 90(10):1054-1062.

(Continued)

*Primary Examiner* — Ileana Popa
(74) *Attorney, Agent, or Firm* — Browdy and Neimark, PLLC

(57) ABSTRACT

The present invention relates to an isolated transgenic pig beta cell wherein the PKC and the PKA pathway are constitutively activated; to a transgenic pig islet comprising said transgenic pig beta cell; and to a transgenic pig comprising said transgenic pig beta cell or said transgenic pig islet. Another object of the invention is a device comprising a transgenic pig beta cell or a transgenic pig islet of the invention. The present invention also relates to the use of said transgenic pig beta cell, said transgenic pig islet, or said device for treating a disease, disorder or condition related to the impaired function of endocrine pancreas or of beta cell.

18 Claims, 4 Drawing Sheets

Specification includes a Sequence Listing.

(56) References Cited

OTHER PUBLICATIONS

Dufrane et al., "Parameters favouring successful adult pig islet isolations for xenotransplantation in pig-to-primate models" Xenotransplantation, 2006, 13:204-214.
Dufrane et al., "Six-Month Survival of Microencapsulated Pig Islets and Alginate Biocompatibility in Primates: Proof of Concept" Transplantation, 2006, 81(9):1345-1353.
Galli et al., "Introduction to Cloning by Nuclear Transplantation" Cloning Stem Cells, 2003, 5:223-232.
Garcia et al, "Glucose-, calcium- and concentration-dependence of acetylcholine stimulation of insulin release and ionic fluxes in mouse islets" Biochem J., 1988, 254:211-218.
McClenaghan et al "Engineering cultured insulin-secreting pancreatic B-cell lines" Journal of Molecular Medicine, 1999, 77(1):235-243.
Mourad, et al., Metabolic amplifying pathway increases both phases of insulin secretion independently of β-cell actin microfilaments, Am. J. Physiol. Cell Physiol., 2010, pp. C389-C398, vol. 299.
Mourad, et al., Metabolic amplification of insulin secretion by glucose is independent of β-cell microtubules, Am. J. Physiol. Cell Physiol., 2011, p. C697-C706, vol. 300.
Mueller et al. "Differences in glucose-stimulated insulin secretion in vitro of islets from human, nonhuman primate, and porcine origin" Xenotransplantation, 2013, 20:75-81.
O'Neil et al., "The isolation and function of porcine islets from market weight pigs" Cell Transplantation, 2001, 10:235-246.
Ramos et al, "Glucose and GLP-1 Stimulate cAMP Production via Distinct Adenylyl Cyclases in INS-1E Insulinoma Cells" J Gen Physiol, 2008, 132(3):329-338.
Ricordi et al. "A Method for the Mass Isolation of Islets From the Adult Pig Pancreas" Diabetes, 1986, 35:649-653.
Vajita et al., "New Method for Culture of Zona-Included or Zona-Free Embryos: The Well of the Well (WOW) System" Molecular Reproduction and Development, 2000, 55:256-64.
Vajita et al., "Handmade Somatic Cell Cloning in Cattle: Analysis of Factors Contributing to High Efficiency In Vitro" Biology of reproduction, 2003, 68:571-8.
Wan et al, "Protein Kinase Activation Increases Insulin Secretion by Sensitizing the Secretory Machinery to Ca2+" J. Gen. Physiol., 2004, 124:653-663.
Yang & Gillis, "A Highly Ca2+-sensitive Pool of Granules Is Regulated by Glucose and Protein Kinases in Insulin-secreting INS-1 Cells" J. Gen. Physiol., 2004, 124:641-651.
International Search Report of related PCT application PCT/EP2015/057914, dated Jul. 22, 2015.
Gautam et al, "A critical role for β-cell M3 muscarinic acetylcholine receptors in regulating insulin release and blood glucose homeostasis in vivo" Cell Metabolism. 2006, 3(6):449-461.
Yang et al., A Highly Ca2+-sensitive Pool of Granules Is Regulated by Glucose and Protein Kinases in Insulin-secreting INS-1 Cells, J. Gen. Physiol., 124:641-651 (2004).
Sato et al., Relative contribution of Ca2+ dependent and Ca2+ independent mechanisms to the regulation of insulin secretion by glucose. FEBS Letters 421:115-119 (1998).
Hughes et al., Effect of secretagogues on cytosolic free Ca2+ and insulin release at different extracellular Ca2+ concentrations in the hamster clonal beta-cell line HIT-T15. Molecular and Cellular Endocrinology 65:35-41 (1989).

\* cited by examiner

SEQUENCE LISTING

<160> NUMBER OF SEQ ID NOS: 23

<210> SEQ ID NO 1
<211> LENGTH: 590
<212> TYPE: PRT
<213> ORGANISM: Sus scrofa

<400> SEQUENCE: 1

```
Met Thr Leu His Asn Asn Thr Thr Ser Pro Leu Phe Pro Asn Ile
1               5                   10                  15

Ser Ser Ser Trp Ile His Gly Pro Ser Asp Ala Gly Leu Pro Pro Gly
            20                  25                  30

Thr Val Thr His Phe Gly Ser Tyr Asn Ile Ser Gln Ala Ala Gly Asn
                35                  40                  45

Phe Ser Ser Pro Asn Gly Thr Thr Ser Asp Pro Leu Gly Gly His Thr
50                  55                  60

Ile Trp Gln Val Val Phe Ile Ala Phe Leu Thr Gly Ile Leu Ala Leu
65                  70                  75                  80

Val Thr Ile Ile Gly Asn Ile Leu Val Ile Val Ala Phe Lys Val Asn
                85                  90                  95

Lys Gln Leu Lys Thr Val Asn Asn Tyr Phe Leu Leu Ser Leu Ala Cys
                100                 105                 110

Ala Asp Leu Ile Ile Gly Val Ile Ser Met Asn Leu Phe Thr Thr Tyr
                115                 120                 125

Ile Ile Met Asn Arg Trp Ala Leu Gly Asn Leu Ala Cys Asp Leu Trp
                130                 135                 140

Leu Ser Ile Asp Tyr Val Ala Ser Asn Ala Ser Val Met Asn Leu Leu
145                 150                 155                 160

Val Ile Ser Phe Asp Arg Tyr Phe Ser Ile Thr Arg Pro Leu Thr Tyr
                165                 170                 175

Arg Ala Lys Arg Thr Thr Lys Arg Ala Gly Val Met Ile Gly Leu Ala
                180                 185                 190

Trp Val Ile Ser Phe Ile Leu Trp Ala Pro Ala Ile Leu Phe Trp Gln
                195                 200                 205

Tyr Phe Val Gly Lys Arg Thr Val Pro Pro Gly Glu Cys Phe Ile Gln
                210                 215                 220

Phe Leu Ser Glu Pro Thr Ile Thr Phe Gly Thr Ala Ile Ala Ala Phe
225                 230                 235                 240

Tyr Met Pro Val Thr Ile Met Thr Ile Leu Tyr Trp Arg Ile Tyr Lys
                245                 250                 255

Glu Thr Glu Lys Arg Thr Lys Glu Leu Ala Gly Leu Gln Ala Ser Gly
                260                 265                 270

Thr Glu Ala Glu Ala Glu Asn Phe Val His Pro Thr Gly Ser Ser Arg
                275                 280                 285

Ser Cys Ser Ser Tyr Glu Leu Gln Gln Gln Ser Leu Lys Arg Ser Ala
                290                 295                 300

Arg Arg Lys Tyr Gly Arg Cys His Phe Trp Phe Thr Thr Lys Ser Trp
305                 310                 315                 320

Lys Pro Ser Ala Glu Gln Met Asp Gln Asp His Ser Ser Ser Asp Ser
                325                 330                 335

Trp Asn Asn Asn Asp Ala Ala Ala Ser Leu Glu Asn Ser Ala Ser Ser
                340                 345                 350

Asp Glu Glu Asp Ile Gly Ser Glu Thr Arg Ala Ile Tyr Ser Ile Val
                355                 360                 365
```

| | | | | | | | | | | | |
|---|---|---|---|---|---|---|---|---|---|---|---|
| Leu | Lys | Leu | Pro | Gly | His | Ser | Thr | Ile | Leu | Asn | Ser | Thr | Lys | Leu | Pro |
| | | | 370 | | | | 375 | | | | 380 | | | | |

Leu Lys Leu Pro Gly His Ser Thr Ile Leu Asn Ser Thr Lys Leu Pro
    370                 375                 380

Ser Ser Asp Asn Leu Gln Val Pro Glu Glu Leu Gly Thr Val Asp
385                 390                 395                 400

Leu Glu Arg Lys Ala Ser Lys Leu Gln Ala Gln Lys Ser Met Asp Asp
                405                 410                 415

Gly Gly Ser Phe Gln Lys Ser Phe Ser Lys Leu Pro Ile Gln Leu Glu
                420                 425                 430

Ser Ala Val Asp Thr Ala Lys Ala Ser Asp Val Asn Ser Val Gly
                435                 440                 445

Lys Thr Thr Ala Thr Leu Pro Leu Ser Phe Lys Glu Ala Thr Leu Ala
    450                 455                 460

Lys Arg Phe Ala Leu Lys Thr Arg Ser Gln Ile Thr Lys Arg Lys Arg
465                 470                 475                 480

Met Ser Leu Ile Lys Glu Lys Ala Ala Gln Thr Leu Ser Ala Ile
                485                 490                 495

Leu Leu Ala Phe Ile Ile Thr Trp Thr Pro Tyr Asn Ile Met Val Leu
                500                 505                 510

Val Asn Thr Phe Cys Asp Ser Cys Ile Pro Lys Thr Tyr Trp Asn Leu
    515                 520                 525

Gly Tyr Trp Leu Cys Tyr Ile Asn Ser Thr Val Asn Pro Val Cys Tyr
                530                 535                 540

Ala Leu Cys Asn Lys Thr Phe Arg Thr Thr Phe Lys Met Leu Leu Leu
545                 550                 555                 560

Cys Gln Cys Asp Lys Arg Lys Arg Arg Lys Gln Gln Tyr Gln Gln Arg
                565                 570                 575

Gln Ser Val Ile Phe His Lys Arg Val Pro Glu Gln Ala Leu
                580                 585                 590

<210> SEQ ID NO 2
<211> LENGTH: 1773
<212> TYPE: DNA
<213> ORGANISM: Sus scrofa

<400> SEQUENCE: 2

```
atgaccttgc acaataacaa tacaacctca cctttgtttc aaacatcag ctcttcctgg    60 attcacggcc cttccgatgc agggctgccc ccaggaacgg ttactcattt tggcagctac   120
aacatttctc aggcagctgg gaatttctcc tctccaaatg caccaccag tgaccctctg   180 ggaggtcaca ccatctggca agtggtgttc attgcattct taacaggcat cctggccttg   240
gtgactatca tcggcaatat cctggtgatc gtggcattca aggtcaacaa gcaactgaag   300
acagtcaaca actacttcct cttaagtctg gcctgtgctg acctgattat cggggtcatt   360
tcaatgaatc tgtttactac ctacatcatc atgaatcgat gggctttagg gaacttggcc   420
tgtgacctct ggctttccat tgactatgtg ctagcaatg cctcggtcat gaatcttctg   480
gtcattagct ttgacaggta cttttccatc acgaggccgc tcacataccg agccaaaaga   540
acaacaaagc gagctggtgt gatgataggt ctggcttggg tcatctcctt catcctttgg   600
gctcctgcca tcttgttctg gcaatacttt gttgggaaga aactgtccc tcaggagag   660 tgtttcatcc agttcctcag tgagcccacc atcaccttcg gcacggccat cgctgccttt   720
tatatgcctg tcaccattat gactatttta tactggagga tctataagga aactgaaaaa   780
cgtaccaaag agcttgccgg gctgcaagcc tctgggacag aggcagaggc agaaaacttt   840
gttcacccca caggtagttc tcggagctgc agcagctatg agcttcagca gcaaagcctg   900
```

```
aaacgctcag ccaggaggaa gtatggacgc tgccacttct ggttcacaac caagagctgg      960
aagcccagtg ctgagcagat ggaccaagac cacagcagca gtgacagctg gaataacaat     1020
gatgctgctg cctccctgga aaactccgcc tcctccgatg aggaggacat tggctcagaa     1080
acaagagcca tctactccat cgtgctcaag cttccaggtc acagcaccat cctcaactcc     1140
accaagttac cgtcttcaga caacctgcag gtgcccgagg aggagctggg acagtggac      1200 ttggagagaa aagccagcaa actgcaagcc agaagagca tggacgatgg aggcagtttt     1260
caaaaaagct ctccaagct tcccatccag ttagagtcag ccgtggacac agccaaggcc     1320
tctgatgtca actcctcagt gggtaagacc acggccactc tacctctgtc ctttaaggaa     1380
gctactctgg ccaagaggtt tgctctgaag accagaagtc agatcaccaa gcggaaacgg     1440
atgtcgctca tcaaggagaa gaaagcggcc cagaccctca cgccatctt gcttgccttc     1500 atcatcacct ggaccccta caatatcatg gttctggtga cacctttg tgacagctgc       1560 atacccaaaa cctattggaa tctgggctac tggctgtgct acatcaacag caccgtgaac     1620
cccgtgtgct atgccctgtg caacaaaaca ttcagaacca ctttcaagat gctgctgctg     1680
tgccagtgtg acaaaaggaa gaggcgcaag cagcagtatc agcaaagaca gtcagtcatt     1740
ttccacaagc gggtgcccga gcaggccttg tag                                 1773

<210> SEQ ID NO 3
<211> LENGTH: 1185
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Constitutively activated type 3 muscarinic
      receptor

<400> SEQUENCE: 3
atgaccttgc acaataacaa tacaacctca cctttgtttc aaacatcag ctcttcctgg       60 attcacggcc cttccgatgc agggctgccc ccaggaacgg ttactcattt tggcagctac     120
aacatttctc aggcagctgg gaatttctcc tctccaaatg caccaccag tgaccctctg      180 ggaggtcaca ccatctggca agtggtgttc attgcattct aacaggcat cctggccttg     240 gtgactatca tcggcaatat cctggtgatc gtggcattca aggtcaacaa gcaactgaag     300
acagtcaaca actactttcct cttaagtctg gcctgtgctg acctgattat cggggtcatt     360
tcaatgaatc tgttactac ctacatcatc atgaatcgat gggctttagg gaacttggcc      420
tgtgacctct ggcttccat tgactatgtg ctagcaatg cctcggtcat gaatcttctg       480
gtcattagct ttgacaggta cttttccatc acgaggccgc tcacataccg agccaaaaga    540
acaacaaagc gagctggtgt gatgataggt ctggcttggg tcatctcctt catcctttgg     600
gctcctgcca tcttgttctg gcaatactt gttgggaaga aactgtccc tccaggagag      660 tgtttcatcc agttcctcag tgagcccacc atcaccttcg gcacggccat cgctgccttt    720
tatatgcctg tcaccattat gactatttta tactggagga tctataagga aactgaaaaa     780
cgtaccaaag agcttgccgg gctgcaagcc tctgggacag agaccagaag tcagatcacc    840
aagcggaaac ggatgtcgct catcaaggag aagaaagcgg ccctgaccct cagcgccatc     900
ttgcttgcct tcatcatcac ctggacccc tacaatatca tggttctggt gaacaccttt     960
tgtgacagct gcataccaa aacctattgg aatctgggct actggctgtg ctacatcaac    1020
```

```
agcaccgtga accccgtgtg ctatgccctg tgcaacaaaa cattcagaac cactttcaag      1080
atgctgctgc tgtgccagtg tgacaaaagg aagaggcgca agcagcagta tcagcaaaga      1140
cagtcagtca ttttccacaa gcgggtgccc gagcaggcct tgtag                      1185
```

<210> SEQ ID NO 4
<211> LENGTH: 394
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: constitutively activated type 3 muscarinic
      receptor

<400> SEQUENCE: 4

```
Met Thr Leu His Asn Asn Asn Thr Thr Ser Pro Leu Phe Pro Asn Ile
1               5                   10                  15

Ser Ser Ser Trp Ile His Gly Pro Ser Asp Ala Gly Leu Pro Pro Gly
            20                  25                  30

Thr Val Thr His Phe Gly Ser Tyr Asn Ile Ser Gln Ala Ala Gly Asn
        35                  40                  45

Phe Ser Ser Pro Asn Gly Thr Thr Ser Asp Pro Leu Gly Gly His Thr
    50                  55                  60

Ile Trp Gln Val Val Phe Ile Ala Phe Leu Thr Gly Ile Leu Ala Leu
65                  70                  75                  80

Val Thr Ile Ile Gly Asn Ile Leu Val Ile Val Ala Phe Lys Val Asn
                85                  90                  95

Lys Gln Leu Lys Thr Val Asn Asn Tyr Phe Leu Leu Ser Leu Ala Cys
            100                 105                 110

Ala Asp Leu Ile Ile Gly Val Ile Ser Met Asn Leu Phe Thr Thr Tyr
        115                 120                 125

Ile Ile Met Asn Arg Trp Ala Leu Gly Asn Leu Ala Cys Asp Leu Trp
    130                 135                 140

Leu Ser Ile Asp Tyr Val Ala Ser Asn Ala Ser Val Met Asn Leu Leu
145                 150                 155                 160

Val Ile Ser Phe Asp Arg Tyr Phe Ser Ile Thr Arg Pro Leu Thr Tyr
                165                 170                 175

Arg Ala Lys Arg Thr Thr Lys Arg Ala Gly Val Met Ile Gly Leu Ala
            180                 185                 190

Trp Val Ile Ser Phe Ile Leu Trp Ala Pro Ala Ile Leu Phe Trp Gln
        195                 200                 205

Tyr Phe Val Gly Lys Arg Thr Val Pro Pro Gly Glu Cys Phe Ile Gln
    210                 215                 220

Phe Leu Ser Glu Pro Thr Ile Thr Phe Gly Thr Ala Ile Ala Ala Phe
225                 230                 235                 240

Tyr Met Pro Val Thr Ile Met Thr Ile Leu Tyr Trp Arg Ile Tyr Lys
                245                 250                 255

Glu Thr Glu Lys Arg Thr Lys Glu Leu Ala Gly Leu Gln Ala Ser Gly
            260                 265                 270

Thr Glu Thr Arg Ser Gln Ile Thr Lys Arg Lys Arg Met Ser Leu Ile
        275                 280                 285

Lys Glu Lys Lys Ala Ala Gln Thr Leu Ser Ala Ile Leu Leu Ala Phe
    290                 295                 300

Ile Ile Thr Trp Thr Pro Tyr Asn Ile Met Val Leu Val Asn Thr Phe
305                 310                 315                 320
```

Cys Asp Ser Cys Ile Pro Lys Thr Tyr Trp Asn Leu Gly Tyr Trp Leu
              325                 330                 335

Cys Tyr Ile Asn Ser Thr Val Asn Pro Val Cys Tyr Ala Leu Cys Asn
              340                 345                 350

Lys Thr Phe Arg Thr Thr Phe Lys Met Leu Leu Leu Cys Gln Cys Asp
              355                 360                 365

Lys Arg Lys Arg Arg Lys Gln Gln Tyr Gln Gln Arg Gln Ser Val Ile
              370                 375                 380

Phe His Lys Arg Val Pro Glu Gln Ala Leu
385                 390

<210> SEQ ID NO 5
<211> LENGTH: 93
<212> TYPE: DNA
<213> ORGANISM: Sus scrofa

<400> SEQUENCE: 5
catgctgaag ggacctttac cagtgatgta agttcttatt tggaaggcca agctgccaag    60
gaattcattg cttggctggt gaaaggccga gga                                 93

<210> SEQ ID NO 6
<211> LENGTH: 31
<212> TYPE: PRT
<213> ORGANISM: Sus scrofa

<400> SEQUENCE: 6

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
              20                  25                  30

<210> SEQ ID NO 7
<211> LENGTH: 60
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Ig K-chain secretion signal

<400> SEQUENCE: 7
gagacagaca cactcctgct atgggtactg ctgctctggg ttccaggttc cactggtgac    60

<210> SEQ ID NO 8
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Ig K-chain secretion signal

<400> SEQUENCE: 8

Glu Thr Asp Thr Leu Leu Leu Trp Val Leu Leu Leu Trp Val Pro Gly
1               5                   10                  15

Ser Thr Gly Asp
              20

<210> SEQ ID NO 9
<211> LENGTH: 171

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A8S GLP-1 with Ig K-chain secretion signal

<400> SEQUENCE: 9
atggagacag acacactcct gctatgggta ctgctgctct ggttccagg ttccactggt    60 gaccggggca ggcggcattc cgaagggacc tttaccagtg atgtaagttc ttatttggaa   120
ggccaagctg ccaaggaatt cattgcttgg ctggtgaaag ccgaggata g              171

<210> SEQ ID NO 10
<211> LENGTH: 56
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A8S GLP-1 with Ig K-chain secretion signal

<400> SEQUENCE: 10

Met Glu Thr Asp Thr Leu Leu Leu Trp Val Leu Leu Leu Trp Val Pro
1               5                   10                  15

Gly Ser Thr Gly Asp Arg Gly Arg Arg His Ser Glu Gly Thr Phe Thr
            20                  25                  30

Ser Asp Val Ser Ser Tyr Leu Glu Gly Gln Ala Ala Lys Glu Phe Ile
        35                  40                  45

Ala Trp Leu Val Lys Gly Arg Gly
    50                  55

<210> SEQ ID NO 11
<211> LENGTH: 1496
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Pig Insulin Promoter

<400> SEQUENCE: 11
gagttcagct gagctggctc ccaggtcacc tctctgggtc ttggtgcccc cagcatctcc    60
caggctggcc ctgccctggg ggtgcccttc ccaccctgcc ctgggccttg tggagggcac   120
cctgggctca ctgggaggcg gtcggccctt ccttcccgc aggatgtaag caccagccta   180
tcttccaggc cctgcgccct ccctgggtgc cccctcctag cctccagagc cctgactcta   240
ggctcttagg atgtcggtct tggaaaactc ctactcatcc gtcaagaccc tcctgggaaa    300
acccttcctt cccagccccc caccctggat ctgtgccctt tcagcctttg aggccacaaa   360
tgaggctgtt tccaaaggtt ggaggcccct ggaagggct gacggccggc ctcctcccct    420 ccaaccctg ggccctgggc tctgccctca tccagtctcc tgccttgcac accctctcat    480
agaggccccc agatcttccc tggctgcaga cgggcctcag gaccccctgc tgtcctggga   540
agccagggcc cagctccttc ctccgcgtgg ggtggggcct cccacagggg gcctgtcccg   600
ggggggtacc agagggtcac ccccgcacat gggacagcga agggaagcag tatgtcgtgg    660
ggccgggtct gaaaggggtc agcagcaggg gctccaggag caggggcac tgagcggtac     720 ctgggggga ggtggtgggg ccacacccag gagtcctgtg ccccccccac tcccgccgtt    780
```

```
ggagatgaga agcaggggcc agcctgcggg tccctgagtt cagcgcccac ccccccgccg      840
cagcaccccg gggtctcagc aggctgctgt gctgggggcg ggggcgctta tggagccggg      900
agcagccccc ccccacggc ctcggagcat ctctggggcc tcagggatgg accggggtct       960
gcaggcaggt gtcctctcgc gcccccactc cctgggctat aacgtggaag atgcggccca     1020
agcccggtcg gtttggcctt tgtccccagc cagtggggac agcctggccc tcaggctgct     1080
cgttaagact ctaatgacct cgaggccccc agaggcgctg atgacccacg agatgatcc      1140 cgcaggcctg gcagcaggga aatgatccag aaagtgccac ctcagccccc agccatctgc     1200
cacccacctg gaggccctca ggggccgggc gccgggggc aggcgctata aagccggctg      1260
ggcccagccg ccccagccc tctgggacca gctgtgttcc caggccaccg gcaagcaggt      1320 ctgtcccct gggctcccgt cagctgggtc tgggctgtcc tgctggggcc agggcatctc      1380
ggcaggagga cgtgggctcc tctctcggag cccttggggg gtgaggctgg tgggggctgc     1440
aggtgcccct ggctggcctc aacgccgccc gtcccccagg tcctcacccc ccgccc         1496

<210> SEQ ID NO 12
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: HA tag

<400> SEQUENCE: 12
tacccatacg atgttccaga ttacgct                                           27

<210> SEQ ID NO 13
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: HA tag

<400> SEQUENCE: 13

Tyr Pro Tyr Asp Val Pro Asp Tyr Ala
1               5

<210> SEQ ID NO 14
<211> LENGTH: 456
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Rabbit beta globin fragment comprising a polyA
      sequence

<400> SEQUENCE: 14
ctttttccct ctgccaaaaa ttatggggac atcatgaagc cccttgagca tctgacttct       60
ggctaataaa ggaaatttat tttcattgca atagtgtgtt ggaattttt gtgtctctca       120 ctcggaagga catatgggag ggcaaatcat ttaaaacatc agaatgagta tttggtttag      180
agtttggcaa catatgccat atgctggctg ccatgaacaa aggtggctat aaagaggtca      240
tcagtatatg aaacagcccc ctgctgtcca ttccttattc catagaaaag ccttgacttg      300
```

```
aggttagatt ttttttatat tttgttttgt gttattttt tctttaacat ccctaaaatt    360
ttccttacat gttttactag ccagattttt cctcctctcc tgactactcc cagtcatagc    420
tgtccctctt ctcttatgaa gatccctcga cctgca                              456
```

<210> SEQ ID NO 15
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: GLP-1 - Forward primer

<400> SEQUENCE: 15

```
cccgcccaat tgatggagac                                                 20
```

<210> SEQ ID NO 16
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: GLP-1 - Reverse primer

<400> SEQUENCE: 16

```
tcctcggcct ttcaccagcc                                                 20
```

<210> SEQ ID NO 17
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: M3R-Forward primer

<400> SEQUENCE: 17

```
cccaattgat gtacccatac                                                 20
```

<210> SEQ ID NO 18
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: M3R - Reverse Primer

<400> SEQUENCE: 18

```
gtgatctgac ttctggtctc                                                 20
```

<210> SEQ ID NO 19
<211> LENGTH: 93
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A8S GLP-1

<400> SEQUENCE: 19

```
cattccgaag ggacctttac cagtgatgta agttcttatt tggaaggcca agctgccaag        60
gaattcattg cttggctggt gaaaggccga gga                                     93
```

```
<210> SEQ ID NO 20
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A8S GLP-1

<400> SEQUENCE: 20

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 21
<211> LENGTH: 403
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: HA-Tagged mutated type 3 muscarinic receptor

<400> SEQUENCE: 21

Met Tyr Pro Tyr Asp Val Pro Asp Tyr Ala Thr Leu His Asn Asn Asn
1               5                   10                  15

Thr Thr Ser Pro Leu Phe Pro Asn Ile Ser Ser Ser Trp Ile His Gly
            20                  25                  30

Pro Ser Asp Ala Gly Leu Pro Pro Gly Thr Val Thr His Phe Gly Ser
        35                  40                  45

Tyr Asn Ile Ser Gln Ala Ala Gly Asn Phe Ser Ser Pro Asn Gly Thr
    50                  55                  60

Thr Ser Asp Pro Leu Gly Gly His Thr Ile Trp Gln Val Val Phe Ile
65                  70                  75                  80

Ala Phe Leu Thr Gly Ile Leu Ala Leu Val Thr Ile Ile Gly Asn Ile
                85                  90                  95

Leu Val Ile Val Ala Phe Lys Val Asn Lys Gln Leu Lys Thr Val Asn
            100                 105                 110

Asn Tyr Phe Leu Leu Ser Leu Ala Cys Ala Asp Leu Ile Ile Gly Val
        115                 120                 125

Ile Ser Met Asn Leu Phe Thr Thr Tyr Ile Ile Met Asn Arg Trp Ala
    130                 135                 140

Leu Gly Asn Leu Ala Cys Asp Leu Trp Leu Ser Ile Asp Tyr Val Ala
145                 150                 155                 160

Ser Asn Ala Ser Val Met Asn Leu Leu Val Ile Ser Phe Asp Arg Tyr
                165                 170                 175

Phe Ser Ile Thr Arg Pro Leu Thr Tyr Arg Ala Lys Arg Thr Thr Lys
            180                 185                 190

Arg Ala Gly Val Met Ile Gly Leu Ala Trp Val Ile Ser Phe Ile Leu
        195                 200                 205

Trp Ala Pro Ala Ile Leu Phe Trp Gln Tyr Phe Val Gly Lys Arg Thr
    210                 215                 220
```

| | | | | | | | | | | | | |
|---|---|---|---|---|---|---|---|---|---|---|---|---|
|Val|Pro|Pro|Gly|Glu|Cys|Phe|Ile|Gln|Phe|Leu|Ser|Glu|Pro|Thr|Ile|
|225| | | | |230| | | | |235| | | | |240|

Thr Phe Gly Thr Ala Ile Ala Ala Phe Tyr Met Pro Val Thr Ile Met
                 245                 250                 255

Thr Ile Leu Tyr Trp Arg Ile Tyr Lys Glu Thr Glu Lys Arg Thr Lys
        260                 265                 270

Glu Leu Ala Gly Leu Gln Ala Ser Gly Thr Glu Thr Arg Ser Gln Ile
          275                 280                 285

Thr Lys Arg Lys Arg Met Ser Leu Ile Lys Glu Lys Lys Ala Ala Gln
 290                 295                 300

Thr Leu Ser Ala Ile Leu Leu Ala Phe Ile Ile Thr Trp Thr Pro Tyr
305                 310                 315                 320

Asn Ile Met Val Leu Val Asn Thr Phe Cys Asp Ser Cys Ile Pro Lys
          325                 330                 335

Thr Tyr Trp Asn Leu Gly Tyr Trp Leu Cys Tyr Ile Asn Ser Thr Val
              340                 345                 350

Asn Pro Val Cys Tyr Ala Leu Cys Asn Lys Thr Phe Arg Thr Thr Phe
          355                 360                 365

Lys Met Leu Leu Leu Cys Gln Cys Asp Lys Arg Lys Arg Arg Lys Gln
370                 375                 380

Gln Tyr Gln Gln Arg Gln Ser Val Ile Phe His Lys Arg Val Pro Glu
385                 390                 395                 400

Gln Ala Leu

```
<210> SEQ ID NO 22
<211> LENGTH: 3169
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Constitutively activated type 3 muscarinic
      receptor - Vector

<400> SEQUENCE: 22
```

| | | | | |
|---|---|---|---|---|
|gagttcagct|gagctggctc|ccaggtcacc|tctctgggtc|ttggtgcccc cagcatctcc|60|
|caggctggcc|ctgccctggg|ggtgcccttc|ccaccctgcc|ctgggccttg tggagggcac|120|
|cctgggctca|ctgggaggcg|tcggcccttt|ccttcccgc|aggatgtaag caccagccta|180|
|tcttccaggc|cctgcgccct|cctgggtgc|cccctccta|cctccagagc cctgactcta|240|
|ggctcttagg|atgtcggtct|tggaaaactc|tactcatcc|gtcaagaccc tcctgggaaa|300|
|acccttcctt|cccagccccc|caccctggat|ctgtgccctt|tcagcctttg aggccacaaa|360|
|tgaggctgtt|tccaaaggtt|ggaggcccct|gggaagggct|gacggccggc tcctcccct|420|
|ccaacccctg|ggccctgggc|tctgccctca|tccagtctcc|tgccttgcac accctctcat|480|
|agaggccccc|agatcttccc|tggctgcaga|cgggcctcag|gaccccctgc tgtcctggga|540|
|agccagggcc|cagctccttc|ctccgcgtgg|ggtggggcct|cccacagggg gcctgtcccg|600|
|gggggtacc|agagggtcac|ccccgcacat|gggacagcga|agggaagcag tatgtcgtgg|660|
|ggccgggtct|gaaaggggtc|agcagcaggg|gctccaggag|gcaggggcac tgagcggtac|720|
|ctgggggga|ggtggtgggg|ccacacccag|gagtcctgtg|ccccccccac tcccgccgtt|780|
|ggagatgaga|agcaggggcc|agcctgcggg|tccctgagtt|cagcgcccac ccccccgccg|840|
|cagcacccg|gggtctcagc|aggctgctgt|gctgggggcg ggggcgctta tggagccggg|900|

```
agcagccccc cccccacggc ctcggagcat ctctggggcc tcaggatgg accggggtct       960
gcaggcaggt gtcctctcgc gcccccactc cctgggctat aacgtggaag atgcggccca     1020
agcccggtcg gtttggcctt tgtccccagc cagtggggac agcctggccc tcaggctgct     1080
cgttaagact ctaatgacct cgaggccccc agaggcgctg atgacccacg agatgatcc      1140
cgcaggcctg gcagcaggga aatgatccag aaagtgccac ctcagccccc agccatctgc     1200
cacccacctg gaggccctca ggggccgggc gccgggggc aggcgctata agccggctg       1260
ggcccagccg ccccagccc tctgggacca gctgtgttcc caggccaccg gcaagcaggt      1320
ctgtcccct gggctccgt cagctgggtc tgggctgtcc tgctggggcc agggcatctc       1380
ggcaggagga cgtgggctcc tctctcggag cccttggggg gtgaggctgg tgggggctgc     1440
aggtgccct ggctggcctc aacgccgcc gtccccagg tcctcaccc ccgcccaatt         1500
gatgtaccca tacgatgttc cagattacgc taccttgcac aataacaata caacctcacc     1560
tttgtttcca aacatcagct cttcctggat tcacggccct tccgatgcag ggctgccccc     1620
aggaacggtt actcattttg gcagctacaa catttctcag gcagctggga atttctcctc     1680
tccaaatggc accaccagtg accctctggg aggtcacacc atctggcaag tggtgttcat     1740
tgcattctta acaggcatcc tggccttggt gactatcatc ggcaatatcc tggtgatcgt     1800
ggcattcaag gtcaacaagc aactgaagac agtcaacaac tacttcctct taagtctggc     1860
ctgtgctgac ctgattatcg gggtcatttc aatgaatctg tttactacct acatcatcat     1920
gaatcgatgg gctttaggga acttggcctg tgacctctgg ctttccattg actatgtggc     1980
tagcaatgcc tcggtcatga atcttctggt cattagcttt gacaggtact tttccatcac     2040
gaggccgctc acataccgag ccaaaagaac aacaaagcga gctggtgtga tgataggtct     2100
ggcttgggtc atctccttca tcctttgggc tcctgccatc ttgttctggc aatactttgt     2160
tgggaagaga actgtccctc aggagagtg tttcatccag ttcctcagtg agcccaccat     2220
caccttcggc acgccatcg ctgccttta tatgcctgtc accattatga ctattttata     2280
ctggaggatc tataaggaaa ctgaaaaacg taccaaagag cttgccgggc tgcaagcctc    2340
tgggacagag accagaagtc agatcaccaa gcggaaacgg atgtcgctca tcaaggagaa    2400
gaaagcggcc ctgaccctca gcgccatctt gcttgccttc atcatcacct ggacccccta    2460
caatatcatg gttctggtga acaccttttg tgacagctgc ataccaaaa cctattggaa     2520
tctgggctac tggctgtgct acatcaacag caccgtgaac ccgtgtgct atgccctgtg    2580
caacaaaaca ttcagaacca cttttcaagat gctgctgctg tgccagtgtg acaaaaggaa   2640
gaggcgcaag cagcagtatc agcaaagaca gtcagtcatt ttccacaagc gggtgcccga   2700
gcaggccttg tagctttttc cctctgccaa aaattatggg gacatcatga agccccttga   2760
gcatctgact tctggctaat aaaggaaatt tattttcatt gcaatagtgt gttggaattt   2820
tttgtgtctc tcactcggaa ggacatatgg gagggcaaat catttaaaac atcagaatga   2880
gtatttggtt tagagtttgg caacatatgc catatgctgg ctgccatgaa caaaggtggc   2940
tataaagagg tcatcagtat atgaaacagc cccctgctgt ccattcctta ttccatagaa   3000
aagccttgac ttgaggttag attttttta tattttgttt tgtgttattt ttttctttaa    3060
catccctaaa attttcctta catgttttac tagccagatt tttcctcctc tcctgactac    3120
tcccagtcat agctgtccct cttctcttat gaagatccct cgacctgca              3169
```

<210> SEQ ID NO 23
<211> LENGTH: 2131

<212> TYPE: DNA
<213> ORGANISM: Artificial Sequence
<220> FEATURE:
<223> OTHER INFORMATION: Synthetic

<400> SEQUENCE: 23

```
gagttcagct gagctggctc ccaggtcacc tctctgggtc ttggtgcccc cagcatctcc      60
caggctggcc ctgccctggg ggtgcccttc ccaccctgcc ctgggccttg tggagggcac     120
cctgggctca ctgggaggcg gtcggccctt tccttcccgc aggatgtaag caccagccta     180
tcttccaggc cctgcgccct ccctgggtgc ccccctccta cctccagagc cctgactcta     240
ggctcttagg atgtcggtct tggaaaactc tactcatcc gtcaagaccc tcctgggaaa      300
accttccttt cccagccccc caccctggat ctgtgccctt tcagcctttg aggccacaaa     360
tgaggctgtt tccaaaggtt ggaggcccct gggaagggct gacggccggc ctcctcccct     420
ccaaccctg ggccctgggc tctgccctca tccagtctcc tgccttgcac accctctcat      480
agaggccccc agatcttccc tggctgcaga cgggcctcag gacccctgc tgtcctggga      540
agccagggcc cagctccttc ctccgcgtgg ggtggggcct cccacaggg gcctgtcccg      600
ggggggtacc agagggtcac ccccgcacat gggacagcga agggaagcag tatgtcgtgg     660
ggccgggtct gaaagggtc agcagcaggg gctccaggag gcagggcac tgagcggtac       720
ctggggggga ggtggtgggg ccacacccag gagtcctgtg ccccccccac tcccgccgtt     780
ggagatgaga agcaggggcc agcctgcggg tccctgagtt cagcgcccac ccccccgccg     840
cagcaccccg gggtctcagc aggctgctgt gctgggggcg ggggcgctta tggagccggg     900
agcagccccc ccccacggc ctcggagcat ctctggggcc tcaggatgg accggggtct       960
gcaggcaggt gtcctctcgc gcccccactc cctgggctat aacgtggaag atgcggccca    1020
agcccggtcg gtttggcctt tgtccccagc cagtggggac agcctggccc tcaggctgct    1080
cgttaagact ctaatgacct cgaggccccc agaggcgctg atgacccacg agatgatcc     1140
cgcaggcctg gcagcaggga aatgatccag aaagtgccac ctcagccccc agccatctgc    1200
cacccacctg gaggccctca ggggccgggc gccgggggc aggcgctata aagccggctg     1260
ggcccagccg ccccagccc tctgggacca gctgtgttcc caggccaccg gcaagcaggt    1320
ctgtccccct gggctcccgt cagctgggtc tgggctgtcc tgctggggcc agggcatctc    1380
ggcaggagga cgtgggctcc tctctcggag cccttggggg gtgaggctgg tgggggctgc    1440
aggtgcccct ggctggcctc aacgccgccc gtccccagg tcctcacccc ccgcccaatt    1500
gatggagaca gacacactcc tgctatgggt actgctgctc tgggttccag gttccactgg    1560
tgaccggggc aggcggcatt ccgaagggac ctttaccagt gatgtaagtt cttatttgga    1620
aggccaagct gccaaggaat tcattgcttg gctggtgaaa ggccgaggat aggatctttt    1680
tccctctgcc aaaaattatg gggacatcat gaagcccctt gagcatctga cttctggcta    1740
ataaaggaaa tttattttca ttgcaatagt gtgttggaat tttttgtgtc tctcactcgg    1800
aaggacatat gggagggcaa atcatttaaa acatcagaat gagtatttgg tttagagttt    1860
ggcaacatat gccatatgct ggctgccatg aacaaaggtg gctataaaga ggtcatcagt    1920
atatgaaaca gccccctgct gtccattcct tattccatag aaaagccttg acttgaggtt    1980
agattttttt tatattttgt tttgtgttat ttttttcttt aacatcccta aaatttttcct   2040
tacatgtttt actagccaga ttttcctcc tctcctgact actcccagtc atagctgtcc    2100
ctcttctctt atgaagatcc ctcgacctgc a                                   2131
```

TRANSGENIC PIG ISLETS AND USES THEREOF FOR TREATING DIABETES

FIELD OF INVENTION

The present invention relates to the domain of the treatment of Diabetes. The present invention particularly relates to the treatment of Diabetes by transplantation of islet of Langherans from Pig, wherein the PKA and PKC pathways are transgenically modified, preferably are constitutively activated.

BACKGROUND OF INVENTION

Type I diabetes mellitus, also referred to as insulin-dependent diabetes mellitus (IDDM) or juvenile diabetes, is a chronic disease. The main symptom is a glycemia higher than normal, resulting from the failure of beta cells of the islets of Langerhans to produce insulin. In a vast majority of patients, the beta cells are destroyed by a T-cell mediated autoimmune attack.

Usual treatments consist in daily injections of insulin, in order to compensate the deficit of production by the pancreas. However, while life-saving, treatment with insulin often does not provide sufficient control of blood glucose to prevent life-shortening complications of the disease. Other treatments are thus currently developed. Some are based on pancreas or islets of Langerhans transplantation to restore a normal production of insulin. Allotransplantations (transplantation of organs from human origin to humans) are limited by the shortage of human islet tissues, as well as by the need for several pancreases for each recipient. There is thus a need for alternative sources of insulin-producing cells.

Pig islets represent a promising alternative to human islet transplantation since they can be obtained in large quantities without raising ethical questions. Insulin produced by porcine beta-cells differs from human insulin by only one amino acid and has long been used to treat diabetic humans. Furthermore, genetic modifications of pig cells are technically possible and should solve several problems related to discordant islet xenotransplantation, for example by minimizing both the number of required islets and the risk of thrombosis (Dufrane & Gianello, Transplantation, 2008, 86(6), 753:60). Moreover, immunosuppression in a xeno-transplantation model can be overcome by micro/macroencapsulation methods (Dufrane et al., 2010, Transplantation, 90(10): 1054-1062; WO2007/144389 and WO2010/032242).

Several preclinical pig-to-non-human primate studies have been published during the last decade, with promising results regarding the production of insulin in the recipient (for a list, see Dufrane & Gianello, Transplantation, 2008, 86(6), 753:60). In particular, clinical studies are current in human diabetic patients, such as, for example, with the use of the product DIABECELL®, comprising alginate-encapsulated pig islets, developed by Living Cell Technologies.

However, pig islets show a relatively weak response to glucose stimulation. When isolated pig islets are stimulated by increasing glucose concentration from resting (1-2 mM) to stimulatory (8-15 mM) levels, the increase in insulin secretion is between 1.5 and 3-fold (Crowther et al. 1989, Horm. Metabol. Res, 21: 590-595; Bertuzzi et al. 1995, FEBES Letters 379: 21-25; Dufrane et al. 2007, Diabetes & Metabolism 33: 430-438; Mueller et al. 2013, Xenotransplantation, 20: 75-81). In comparison, insulin secretion is increased by 12 to 16-fold when human, primate or rodent islets are challenged with a similar increase in glucose concentration (Dufrane et al. 2007; Mueller et al. 2013). This property of pig islets has sometimes drawn doubts regarding their usefulness as a treatment for diabetes when transplanted into more insulin-demanding organisms such as non-human primates and possibly humans. In particular, the lower response to blood glucose of porcine islets compared to human islets leads to the need of transplanting a high number of pig islets to adequately correct the human glucose level, which is also a drawback of the treatment method as several pigs are currently used to transplant one patient.

There is thus a need for an improved method for treating diabetic patients through the xenotransplantation of pig islet.

In human beta cells, the synthesis and secretion of insulin in response to blood glucose levels may involve two pathways: (i) the PKC pathway, and (ii) the PKA pathway. The Applicant herein surprisingly showed that the constitutive activation of both pathways leads to a synergistic increase of insulin secretion. This result was particularly unexpected, as it was previously shown in the prior art that the effects of PKC and PKA on insulin secretion in mice were not even additive (Yang & Gillis, J. Gen. Physiol., 2004, 124:641-651; Wan et al, J; Gen. Physiol., 2004, 124:653-663).

The present invention thus relates to a transgenic pig beta cell, to a transgenic pig islet and to a transgenic pig wherein the PKC and PKA pathways are constitutively activated, and to the uses thereof for treating Diabetes in a subject in need thereof.

SUMMARY

The present invention thus relates to an isolated transgenic pig beta cell wherein the PKC and the PKA pathway are constitutively activated.

In one embodiment, the cell comprises a constitutively active acetylcholine receptor, preferably muscarinic receptor, more preferably type III muscarinic receptor. In one embodiment, the constitutively active type III muscarinic receptor has an amino acid sequence SEQ ID NO: 4, or a sequence having at least 70% sequence identity with SEQ ID NO: 4.

In one embodiment, the cell expresses GLP-1. In one embodiment, GLP1 has the amino acid sequence SEQ ID NO: 6, or a sequence having at least 70% sequence identity with SEQ ID NO: 6.

The present invention also relates to an isolated transgenic pig islet comprising a pig beta cell of the invention.

Another object of the invention is an ex vivo method for obtaining an isolated transgenic pig beta cell of the invention or an isolated transgenic pig islet of the invention, wherein said method uses an expression vector comprising a nucleic acid sequence encoding a constitutively active type III muscarinic receptor, and an expression vector comprising a nucleic acid sequence encoding GLP-1.

Another object of the invention is an isolated transgenic pig beta cell or an isolated transgenic pig islet obtained by the ex vivo method for obtaining an isolated transgenic pig beta cell of the invention or an isolated transgenic pig islet of the invention.

The present invention also relates to a transgenic pig comprising an isolated transgenic pig beta cell, or an isolated transgenic pig islet of the invention.

The present invention also relates to a device comprising an isolated transgenic pig beta cell, or an isolated transgenic pig islet of the invention. In one embodiment, said isolated transgenic pig beta cell or said isolated transgenic pig islet are encapsulated in an alginate composition.

Another object of the invention is an isolated transgenic pig beta cell, or an isolated transgenic pig islet, or a device of the invention, for treating a disease, disorder or condition related to the impaired function of endocrine pancreas or beta cell. In one embodiment, said disease, disorder or condition related to the impaired function of endocrine pancreas or beta cell is selected from the group comprising type I diabetes, type II diabetes, gestational diabetes, latent autoimmune diabetes, type 1.5 diabetes, lipoatrophic diabetes, maturity onset diabetes of the young, neonatal diabetes (e.g. permanent neonatal diabetes or transient neonatal diabetes), prediabetes, steroid-induced diabetes, pancreatic cancer, in particular endocrine pancreas cancer, such as, for example, endocrine pancreatic tumors and pancreatic neuroendocrine carcinomas.

Another object of the invention is an isolated transgenic pig beta cell, or an isolated transgenic pig islet, or a device of the invention, for regulating blood glucose levels in a subject in need thereof.

Another object of the invention is an isolated transgenic pig beta cell, or an isolated transgenic pig islet, or a device of the invention, for restoring normal insulin secretion levels in a subject in need thereof.

Definitions

In the present invention, the following terms have the following meanings:
 "Isolated" refers to an organ, tissue or cell which has been separated from its natural environment and is at least about 75% free, 80% free, 85% free and preferably about 90%, 95%, 96%, 97%, 98%, 99% free, from other cells with which it is naturally present, but which lack the cell surface markers based on which the cells were isolated. The term includes gross physical separation from the natural environment, such as, for example, removal from the donor animal, and alteration of the organ's, tissues, or cell's relationship with its neighboring cells or with which they are in direct contact by dissociation. Isolation methods of a cell population are well known in the art and include, but are not limited to, cell sorting by flow cytometry, magnetic selection, affinity chromatography, panning or combinations thereof.
 "Synergism" defines the interaction of two or more agents acting together in a positive way to produce an effect that is greater than the sum of the effects of each agent operating by itself.
 "About" preceding a figure means plus or less 10% of the value of said figure.
 "Treating" refers to therapeutic treatment; wherein the object is to prevent or slow down (lessen) the targeted pathologic condition or disorder. Those in need of treatment include those already with the disorder. A subject is successfully "treated" for a disease, disorder or condition if, after receiving a therapeutic amount of a transgenic pig islet or pig beta cell of the invention, the subject shows observable and/or measurable reduction in or absence of one or more of the following: improvement of insulin secretion; and/or relief to some extent, of one or more of the symptoms associated with the specific disease or condition; reduced morbidity and mortality, improved glycaemia control and improvement in quality of life issues. The above parameters for assessing successful treatment and improvement in the disease are readily measurable by routine procedures familiar to a physician.

"Therapeutically effective amount" means level or amount of transgenic pig islets or beta cells that is aimed at, without causing significant negative or adverse side effects to the target, (1) slowing down or stopping the progression, aggravation, or deterioration of one or more symptoms of the disease, disorder, or condition associated with a deficiency in or absence of endocrine pancreas or beta cells function; (2) bringing about ameliorations of the symptoms of the disease, disorder, or condition associated with a deficiency in or absence of endocrine pancreas or beta cells function; (3) reducing the severity or incidence of the disease, disorder, or condition associated with a deficiency in or absence of endocrine pancreas or beta cells function; or (4) curing the disease, disorder, or condition associated with a deficiency in or absence of endocrine pancreas or beta cells function. According to the present invention, the therapeutically effective amount is usually administered after initiation of the disease, disorder, or condition associated with a deficiency in or absence of endocrine pancreas or beta cells function, for a therapeutic action.
 "Implanting" or "transplanting" (used interchangeably) refers to the placement of the organs, tissues, cells or compositions into a subject, for example a xenogeneic subject, by a method or route which results in the localization of the organs, tissues, cells or composition at a desired site. As used herein, a xenogeneic subject refers to a recipient into which cells of another species are introduced or are to be introduced. In particular, in the context of the present invention, a xenogeneic subject may refer to a primate, preferably a human, into which pig cells are introduced or are to be introduced.
 "Disease, disorder or condition associated with a deficiency in or absence of endocrine pancreas or beta cells function" includes a disorder in which there is abnormal endocrine pancreas or beta cells function. Such abnormal endocrine pancreas function may include an impairment or absence of the normal endocrine pancreas function or presence of an abnormal endocrine pancreas function. Examples of diseases, disorders or conditions associated with a deficiency in or absence of endocrine pancreas or beta cells function include, but are not limited to, type I diabetes, type II diabetes, gestational diabetes, latent autoimmune diabetes, type 1.5 diabetes, lipoatrophic diabetes, maturity onset diabetes of the young, neonatal diabetes (e.g. permanent neonatal diabetes or transient neonatal diabetes), prediabetes, steroid-induced diabetes, pancreatic cancer, preferably endocrine pancreas cancer, such as, for example, endocrine pancreatic tumors and pancreatic neuroendocrine carcinomas.
 "Regulating blood glucose levels": maintaining blood glucose levels within the parameters for a normal, non-diabetic individual of similar age and weight. In one embodiment, regulating blood glucose levels means restoring a normal fasting blood glucose level. In one embodiment, a normal fasting blood glucose level is under 110 mg/dL (6.1 mmol/L), preferably under 100 mg/dL (5.6 mmol/L).
 "Alginate": salts of alginic acid. Alginic acid, which is isolated from seaweed, is a polyuronic acid made up of two uronic acids: D-mannuronic acid and L-guluronic acid. Alginic acid is substantially insoluble in water. It forms water-soluble salts with alkali metals, such as sodium, potassium, and, lithium; magnesium; ammonium; and the substituted ammonium cations derived from lower amines, such as methyl amine, ethanol amine, diethanol amine, and triethanol amine. The salts are soluble in aqueous media above pH 4, but are converted to alginic acid when the pH is lowered below about pH 4. A thermo-irreversible water-insoluble alginate gel is formed in the presence of gel-forming ions, e.g. calcium, barium, strontium, zinc, copper(+2), aluminum, and mixtures thereof, at appropriate concentrations. The alginate gels can be solubilized by soaking in a solution of soluble cations or chelating agents for the gel-forming ions, for example EDTA, citrate and the like.

DETAILED DESCRIPTION

The present invention thus relates to a pig beta cell, preferably an isolated pig beta cell, wherein the PKC and PKA pathways are constitutively activated, thereby inducing an increased secretion of insulin by said cells. According to the invention, the constitutive activation of the PKC and PKA pathways results from the transgenic modification of the pig beta cell of the invention.

Pancreatic islets are innervated by parasympathetic, sympathetic and sensory nerves. Thus, insulin secretion is stimulated by the parasympathetic system and inhibited by the sympathetic system. Acetylcholine (ACh) is the main neurotransmitter involved in parasympathetic control of beta-cells, through the PKC pathway. The cephalic phase, i.e. insulin secretion in response to sensory stimuli prior to any increase in blood glucose levels, depends on parasympathetic stimulation that is then sustained during the whole meal. ACh may bind to M3 muscarinic receptors present in the beta-cell plasma membrane. These receptors are coupled (via Gq) to a phosholipase C (PLC) which, upon activation, hydrolyzes membrane phosphoinositides, such as, for example, phosphatidylinositol-4, 5-bisphosphate (PIP2). In islets as in other cells, this hydrolysis results in the formation of two major products: inositol-1, 4, 5-trisphophate (IP3) and diacylglycerol (DAG). DAG may activate the PKC pathway, leading to an enhanced insulin synthesis and secretion. In parallel, IP3 may bind to IP3 sensitive $Ca^{2+}$ channels on the endoplasmic reticulum, thereby inducing the excretion of $Ca^{2+}$ within the cytoplasm, which in turn leads to an enhanced insulin synthesis and secretion. According to the invention, the "PKC pathway" comprises the M3 muscarinic receptors and the downstream elements (Gq proteins, PLC, DAG, PKC . . . ).

Glucagon-like-peptide-1 (GLP-1) is secreted by L-cells from the mucosa of the ileum and colon, and glucose-dependent insulinotropic polypeptide (GIP) is secreted by K-cells from the duodenojejunal mucosa. These two hormones bind to their respective G protein-coupled receptors (GPCRs) and are responsible for the incretin effect that occurs during meals and is experimentally demonstrated by the larger stimulation of insulin secretion when a given glucose load is administered orally rather than being intravenously injected. The effect of these two hormones is mainly mediated by cAMP acting through protein kinase A and Epac2, i.e. the PKA pathway. Glucose transporter-2 (Glut2), the Kir6.2 and SUR1 subunits of K-ATP channels are phosphorylated by PKA, as well as proteins associated with the secretory process. The small GTPase Rapt may be the effector of Epac2-dependent pathway by increasing the number of readily releasable insulin granules particularly during the first phase of glucose-induced insulin secretion.

According to the invention, the "PKA pathway" comprises GLP-1, GPCR and downstream elements (adenylyl cyclase, cAMP, PKA . . . ).

In one embodiment, the constitutive activation of the PKC pathway is due to the constitutive activation of the M3 muscarinic receptor. The constitutive activation of the PKC pathway may thus be verified by measuring inositol triphosphate (IP3) efflux from the cells. Indeed, Phospholipase C activation, resulting in PKC activation, leads to membrane phosphoinositides breakdown into IP3 and diacylglycerol (DAG). In one embodiment, the constitutive activation of the PKC pathway may be verified according to the Test A, wherein Test A comprises a first step of labelling the inositol pools by loading cells with myo-[2-3H] inositol for 2 hours, and a second step of measuring effluent 3H and quantifying the remaining signal in the cells, thereby allowing the verification of PKC pathway activation (Garcia et al, 1988, Biochem J., 254, 211-218).

In one embodiment, the constitutive activation of the PKC pathway induces an increase in total IP3 measured in the conditions of Test A of at least 5 fold, preferably 10, 15, 20, 25 or 30 fold or more compared to control, wherein the control preferably corresponds to cells wherein the PKC pathway is not constitutively activated.

In another embodiment, the constitutive activation of the PKC pathway may be verified by assessing the constitutive activation of PKC by measuring the amount of the phosphorylated form of the protein (phosphorylated PKC is the active form of the enzyme). This can be achieved for example by Western Blot of protein extract from transgenic pig beta cells of the invention. Antibodies that specifically recognize phosphorylated PKC can be used to determine the amount of activated PKC compared to total PKC in transgenic compared to wild-type pig beta cells. Examples of such antibodies include, but are not limited to, ab59411, ab75837, ab76016 and ab32502 (Abcam). In one embodiment, a ratio phosphorylated PKC/non-phosphorylated PKC (i.e. active PKC/inactive PKC) may be measured. In one embodiment, the constitutive activation of PKC results in the 2 fold increase of this ratio, preferably 3, 4, 5, 6, 7, 8, 9, 10 fold or more increase, compared to the ratio measured in wild-type cells.

In one embodiment, as adenylyl cyclase activation leads to cAMP formation from ATP breakdown, the constitutive activation of the PKA pathway may be verified according to the Test B, wherein Test B detects adenylyl cyclase activation by GLP-1 binding to its membrane receptor by measuring total cAMP concentration in beta-cells using commercially available assay kits (Ramos et al, 2008, J Gen Physiol, 132(3): 329-338).

In one embodiment, the constitutive activation of the PKA pathway corresponds to an increase in total cAMP measured in the conditions of Test B of at least 20, 25, 30, or 35 fold or more compared to control, wherein the control preferably corresponds to cells wherein the PKA pathway is not constitutively activated.

In another embodiment, the constitutive activation of the PKA pathway may be verified by assessing the constitutive activation of PKA by measuring the phosphorylated form of the protein (phosphorylated PKA is the active form of the enzyme). This can be achieved for example by Western Blot of protein extract from transgenic pig beta cells of the invention. Antibodies that specifically recognize phosphorylated PKA can be used to determine the amount of activated PKA compared to total PKA in transgenic compared to wild-type pig beta cells. Examples of such antibodies include, but are not limited to, ab5815, ab118531 and ab39218 (Abcam). In one embodiment, a ratio phosphorylated PKA/non-phosphorylated PKA (i.e. active PKA/inactive PKA) may be measured. In one embodiment, the constitutive activation of PKA results in the 2 fold increase of this ratio, preferably 3, 4, 5, 6, 7, 8, 9, 10 fold or more increase, compared to the ratio measured in wild-type cells.

In one embodiment of the invention, the transgenic pig beta cell is capable of secreting at least about 2, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10 fold more, preferably at least 15 fold more, more preferably at least 20 fold more, and even more preferably at least 25 fold more insulin than native pig beta cells in the conditions of Test C.

The method of Test C for determining secretion levels of insulin may be for example the following:
1) overnight culture of the transgenic pig beta cells at 37° C., 5% $CO_2$/95% $O_2$ in RMPI medium containing 10% heat-inactivated FCS, 100 IU/ml penicillin, 100 µg/ml streptomycin, 5 mmol/l glucose,
2) 2 hr incubation of said transgenic pig beta cells in 1 mL of Krebs-Ringer buffer at 1 mmol/L or 15 mmol/L glucose,
3) quantification of insulin in recovered media and in incubated transgenic pig beta cells by radioimmunoassay.

In one embodiment, the constitutive activation of the PKC pathway results from the constitutive activation of an acetylcholine receptor, preferably of a muscarinic receptor, more preferably of a type III muscarinic receptor. In one embodiment, the transgenic pig beta cell comprises a constitutively activated type III muscarinic receptor on its membrane.

The expression of a constitutively activated type III muscarinic receptor on the membrane of a transgenic pig beta cell may be verified by in vitro methods known from the skilled artisan. Examples of such methods include, but are not limited to, Western Blot using either an antibody directed to the type III muscarinic receptor or an antibody directed to a Tag attached to the constitutively activated type III muscarinic receptor sequence (see below for a list of Tags).

In one embodiment, the integration of the constitutively activated type III muscarinic receptor sequence in the genome of a transgenic pig beta cell may be verified by in vitro methods known from the skilled artisan. Examples of such methods include, but are not limited to, RT-PCR, using for example the following pair of primers: Forward primer: 5' CCCAATTGATGTACCCATAC 3' (SEQ ID NO: 17)—Reverse primer: 5' GTGATCTGACTTCTGGTCTC 3' (SEQ ID NO: 18).

The type III muscarinic receptor from pig (Sus scrofa) is an acetylcholine receptor corresponding to the accession numbers NP_001116570.1 (protein sequence, SEQ ID NO: 1) and NM_001123098.1 (cDNA sequence, SEQ ID NO: 2). The activation of the type III muscarinic receptor may induce the activation of the phospholipase C, which hydrolyzes cell membrane phospholipids, leading to the production of diacylglycerol (DAG) and/or of inositol triphosphate (IP3). DAG may activate the PKC pathway, leading to an enhanced insulin synthesis and secretion. In parallel, IP3 may bind to IP3 sensitive $Ca^{2+}$ channels on the endoplasmic reticulum, thereby inducing the excretion of $Ca^{2+}$ within the cytoplasm. Both lead to an enhanced insulin synthesis and secretion.

In one embodiment, the constitutively activated type III muscarinic receptor has the sequence SEQ ID NO: 1 wherein a point mutation (Gln490→Leu, position 490 being positioned in the sequence without the first Met amino acid (corresponding to the start codon) and therefore relates to position 491 of SEQ ID NO: 1) causes constitutive activation and wherein a region is deleted to increase expression. In one embodiment, said deletion comprises amino acids 275 to 470 of SEQ ID NO: 1.

In one embodiment, the constitutively activated type III muscarinic receptor is encoded by a nucleic acid sequence SEQ ID NO: 3, or by a nucleic acid sequence having at least 70%, preferably 75, 80, 85, 90, 95% or more sequence identity with SEQ ID NO: 3. In one embodiment, the constitutively activated type III muscarinic receptor has an amino acid sequence SEQ ID NO: 4, or a sequence having at least 70%, preferably 75, 80, 85, 90, 95% or more sequence identity with SEQ ID NO: 4.

In one embodiment, the constitutively activated type III muscarinic receptor comprises a Tag, such as, for example, an HA tag (having for example the sequence SEQ ID NO: 13, encoded by the nucleotide sequence SEQ ID NO: 12). Preferably, the HA-tagged constitutively activated type III muscarinic receptor has the sequence SEQ ID NO: 21.

The term "identity" or "identical", when used in a relationship between the sequences of two or more nucleic acid sequences or of two or more polypeptides, refers to the degree of sequence relatedness between nucleic acid sequences or polypeptides, as determined by the number of matches between strings of two or more nucleic or amino acid residues, respectively. "Identity" measures the percent of identical matches between the smaller of two or more sequences with gap alignments (if any) addressed by a particular mathematical model or computer program (i.e., "algorithms"). Identity of related nucleic acid sequences or polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988). Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. \2, 387 (1984); Genetics Computer Group, University of Wisconsin, Madison, Wis.), BLASTP, BLASTN, and FASTA (Altschul et al., J. MoI. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

In one embodiment, the constitutive activation of the PKA pathway results from the expression of GLP-1 by the pig beta cell of the invention. In one embodiment, the transgenic pig beta cell comprises a GLP-1 sequence integrated in its genome.

The integration of the GLP-1 sequence in the genome of a transgenic pig beta cell may be verified by in vitro methods known from the skilled artisan. Examples of such methods include, but are not limited to, RT-PCR, using for example the following pair of primers: Forward primer: 5' CCCGCC-CAATTGATGGAGAC 3' (SEQ ID NO: 15)—Reverse primer: 5' TCCTCGGCCTTTCACCAGCC 3' (SEQ ID NO: 16).

In one embodiment, GLP-1 is encoded by a nucleic acid sequence SEQ ID NO: 5, or a nucleic acid sequence having at least 70%, preferably 75, 80, 85, 90, 95% or more sequence identity with SEQ ID NO: 5. In one embodiment, GLP-1 has an amino acid sequence SEQ ID NO: 6, or a sequence having at least 70%, preferably 75, 80, 85, 90, 95% or more sequence identity with SEQ ID NO: 6.

In one embodiment, the GLP-1 sequence is mutated for enhancing the half-life of GLP-1. In one embodiment, said mutation for enhancing the half-life of GLP-1 corresponds to the substitution of an Alanine residue in position 2 in SEQ ID NO: 6 by a Serine residue (A8S mutation).

In one embodiment, GLP-1 comprises the A8S mutation and is encoded by a nucleic acid sequence SEQ ID NO: 19, or a nucleic acid sequence having at least 70%, preferably 75, 80, 85, 90, 95% or more sequence identity with SEQ ID NO: 19. In one embodiment, GLP-1 comprises the A8S mutation and has an amino acid sequence SEQ ID NO: 20, or a sequence having at least 70%, preferably 75, 80, 85, 90, 95% or more sequence identity with SEQ ID NO: 20.

In one embodiment, the GLP1 sequence further comprises an additional sequence allowing its secretion. In one embodiment, said additional sequence corresponds to Ig K-chain signal (nucleic acid sequence SEQ ID NO: 7, amino acid sequence SEQ ID NO: 8). In one embodiment, the nucleic acid sequence SEQ ID NO: 7 is inserted within the nucleic acid sequence encoding GLP-1, after the first ATG.

In one embodiment, the GLP1 sequence comprises both the A8S mutation and the Ig K-chain signal. According to this embodiment, the amino acid sequence of GLP-1 may be SEQ ID NO: 10, which is encoded by SEQ ID NO: 9.

In one embodiment, the GLP-1 sequence comprises a furin cleavage site inserted between the Igk-chain signal and the CAT encoding the first histidine of the GLP-1 peptide. The presence of this furin site ensures that the synthesized peptide will be processed in the Golgi apparatus and cleaved to produce a bioactive form of GLP-1. The DNA sequence of this furin cleavage site is: CGG GGC AGG CGG, which is included in SEQ ID NO:9. The peptide sequence of this furin cleavage site is: Arg Gly Arg Arg, which is included in SEQ ID NO:10.

The present invention thus relates to a transgenic pig beta cell, preferably to an isolated transgenic pig beta cell, comprising:
- a sequence of a mutated acetylcholine receptor, preferably of a mutated muscarinic receptor, more preferably of a mutated type III muscarinic receptor, and even more preferably the sequence SEQ ID NO: 4, wherein said mutated receptor is constitutively activated; and
- a sequence encoding human GLP-1, preferably having the sequence SEQ ID NO: 10.

In one embodiment, both sequences (the sequence of a mutated acetylcholine receptor and the sequence encoding human GLP-1) are on the same vector (i.e. a bicistronic vector).

The present invention also relates to a transgenic pig islet, preferably an isolated transgenic pig islet, comprising at least one transgenic beta cell as hereinabove described.

In one embodiment of the invention, the transgenic pig islet is capable of secreting at least about 2, 2.5, 2.6, 2.7, 2.8, 2.9, 3, 3.1, 3.2, 3.3, 3.4, 3.5, 3.6, 3.7, 3.8, 3.9, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10 fold more, preferably at least 15 fold more, more preferably 20 fold more, and even more preferably at least 25 fold more insulin than native pig islet in the conditions of Test D.

The method of Test D for determining secretion levels of insulin may be for example the following:
1) overnight culture of the transgenic pig islets at 37° C., 5% $CO_2$/95% $O_2$ in RMPI medium containing 10% heat-inactivated FCS, 100 IU/ml penicillin, 100 μg/ml streptomycin, 5 mmol/l glucose,
2) 2 hr incubation of said transgenic pig islets in 1 mL of Krebs-Ringer buffer at 1 mmol/L or 15 mmol/L glucose,
3) quantification of insulin in recovered media and in incubated islets by radioimmuno-assay.

According to the invention, the transgenic pig islet of the invention comprises transgenic beta cells as hereinabove described.

In one embodiment of the invention, the transgenic pig islet of the invention exhibits the normal physiological structure of a pig islet, with alpha cells located in a ring at the periphery of the islet, while beta cells are located within the hub of the islet. In one embodiment, the transgenic pig islet of the invention has a size ranging from about 50 to 500 μm, preferably from about 150 to 250 μm. In one embodiment, the beta/alpha cells proportion of the transgenic pig islet of the invention ranges from about 5/1 to about 20/1, preferably from about 10/1 to about 12.5/1, more preferably is of about 11.25/1.

The present invention also relates to transgenic pigs comprising at least one transgenic beta cell and/or at least one transgenic pig islet of the invention within the pancreas.

In one embodiment of the invention, the transgenic pigs are free of infectious microorganisms, in order to limit the risks of transmission of a disease during xenotransplantation. As an example, the islets may be extracted from AI pigs described in WO2006/110054, which is incorporated herein by reference. These pigs have been resident on the remote Auckland Island (New Zealand) and are free, or quasi-free, of porcine endogenous retrovirus (PERV) and other common pig infectious viruses including PCMV, PLHV, EMCV, HEV and PCV. Another example is specific pathogen-free (SPF) NZ Large White pigs raised under strict biosecurity.

In one embodiment of the invention, the transgenic modification is carried out in vivo.

In one embodiment, the transgenic modification is carried out ex vivo, in order to generate the transgenic pigs of the invention. Methods for generating transgenic pigs using an ex-vivo method are well-known from the skilled artisan. In one embodiment, the following method may be used for obtaining transgenic pigs:

An expression vector carrying a pig insulin promoter and the sequence of the transgene is developed as described below. Primary Gal$^{-/-}$ and wild type fibroblasts are established from ear biopsy of pigs and cultured in vitro, preferably in DMEM/TCM199 with 10% FCS and 10 ng/ml of FGF in 5% $CO_2$ and 5% $O_2$.

Growing cultures are then transfected. In one embodiment, transfection is carried out by electroporation. In one embodiment, transfection is carried out by chemical transfection. In a preferred embodiment, transfection is carried out by a combination of smart electroporation and chemical transfection, such as, for example using Nucleofector (Amaxa).

Transfected cells are then expanded and frozen for nuclear transfer. An aliquot of said cells may be expanded to perform PCR analysis to determine the integration of the transgene.

Oocytes are recovered from ovaries of slaughtered cycling female at the local slaughterhouse. Selected oocytes are matured in vitro, preferably in medium DMEM/F12 with 10% FCS in presence of gonadotropins for 42-44 h in 5% $CO_2$ at 38.5° C. At the end of maturation, cumulus cells are removed and oocytes with the first polar body are selected for further processing.

In one embodiment of the invention, the method used for nuclear transfer is based on the zona-free system: Zona pellucida is removed by pronase digestion with a short incubation time till zona pellucida starts to dissolve. Zona free oocytes are then stained with Hoechst and exposed to cytochalasine B before enucleation. Oocytes are layered in a row of microdrops individually and enucleated with a blunt micropipette.

In another embodiment of the invention, oocytes are prepared by conventional zona-enclosed method: cells used for nuclear transfer are grown to confluence and/or serum starved for 24-48 h to synchronize their cell cycle. Before manipulation, cells are trypsinised into single cell suspension and kept at room temperature until use. For nuclear transfer, cells are spread at high dilution on a culture dish (drop of medium) just before use, enucleated oocytes are washed first in medium containing phytohemagglutinin and then immediately dropped over a cell and rolled over till there is strong contact between the two units (Vajta et al., 2003, Biology of reproduction, 68:571-8).

Subsequently the couplets (enucleated oocyte-somatic cell) are subjected to cell fusion. The couplets are transferred to an anionic media, preferably containing 0.3 M mannitol, 0.01 mM Mg, PVA and then to a fusion chamber. Fusion is obtained by delivering a double DC pulse (such as, for example, of 1.2 Kv/cm for 30 μsec). Couplets that do not fuse may be re-subjected to a second round of fusion. In one embodiment, fused couplets are activated within 1-2 h after fusion by double DC pulse of 1.2 KV/cm for 30 μsec in the fusion medium containing 1 mM Ca and incubated in 5 μM of cytochalasin B in mSOFaa medium for 3.5-4 h.

After activation the reconstructed zona free embryos may be cultured in the modified "well of the well" system (Vajta et al., 2000, Molecular Reproduction and Development, 55:256-64) in microdrops under mineral oil to prevent adhesion between embryos.

In one embodiment, for in vitro culture 20 μl microdrops of mSOFaa (Galli et al., 2003, Cloning Stem Cells, 5: 223-232) under oil are prepared and then 10 to 15 small depressions are made using a blunt small metal device. In each depression one embryo is accommodated for all the culture period. On day 3 of culture half of the medium is replaced with fresh media. On day 5 embryo development is evaluated. Compacted morula and early blastocysts are transferred to the uterus of synchronised recipients.

Pregnancies may be diagnosed by ultrasound, such as, for example, on day 25 of gestation. In one embodiment, recovered fetuses or newborn animals are subjected to analysis to determine transgene expression in the islets, such as, for example, by immunocytochemistry. In one embodiment, pancreatic cells are stored in liquid nitrogen for future cloning. Based on the transgene expression findings, the best expressing fetuses are subjected to re-cloning to generate the transgenic animals required for the transgenic pig islets isolation. In this case all the pregnancies are allowed to go to term to generate live animals.

According to one embodiment, transgenic modifications are carried out using viral vectors, preferably using viruses, more preferably using viruses selected from the group comprising Lentivirus, such as, for example, HIV vectors with different envelopes: VSV, gammaretroviral (MLV-A, RD114, GALV), Ross River Virus, Rabies, Measles; and Adeno-Associated-Vectors (AAV). In a preferred embodiment, the vector for transgenic modification is a Lentivirus.

According to one embodiment, the gene used for transgenic modification of the pig islet cells is under control of a beta cell specific pig insulin promoter, with or without universal promoters such as UCOE promoters (resistant to silencing), CAGGS promoter (a combination of the cytomegalovirus (CMV) early enhancer element and chicken beta-actin promoter) or CMV (cytomegalovirus) promoter. In one embodiment, the transgene is under the control of a pig insulin promoter, preferably said insulin promoter is specific of beta pig islet cells, leading to an expression of the transgene in beta cells only. An example of nucleic acid sequence of insulin promoter includes, but is not limited to, SEQ ID NO: 11.

In one embodiment, the transgenic protein is fused to an additional sequence. In one embodiment, said additional sequence is fused in C-term of the transgenic protein. In another embodiment, said additional sequence is fused in N-term of the transgenic protein.

In one embodiment, said additional sequence directs the protein to the secretory pathway. Examples of such sequences include, but are not limited to, the Ig K-chain secretion signal (having the amino acid sequence SEQ ID NO: 8, encoded by SEQ ID NO: 7).

In one embodiment, said additional sequence is a tag, allowing for example the identification and isolation of said transgenic protein. Examples of tags are well-known to the skilled artisan, and include, without limitation, Hemagglutinin Tag (HA tag), Poly Arginine Tag, Poly Histidine Tag, Myc Tag, Strep Tag, S-Tag, HAT Tag, 3× Flag Tag, Calmodulin-binding peptide Tag, SBP Tag, Chitin binding domain Tag, GST Tag, Maltose-Binding protein Tag, Fluorescent Protein Tag, T7 Tag, V5 Tag and Xpress Tag. In one embodiment, the transgenic protein comprises a HA tag, such as, for example, a HA tag having the amino acid sequence YPYDVPDYA (SEQ ID NO: 13), encoded by the nucleic acid sequence SEQ ID NO: 12.

In one embodiment, the transgene is fused in its 3' extremity to an additional sequence allowing efficient termination of transcription.

In one embodiment, the transgene is fused to a polyA sequence. In one embodiment, the transgene is fused to a rabbit beta globin fragment comprising a polyA sequence, having for example the sequence SEQ ID NO: 14.

Another object of the invention is a vector comprising the sequence in nucleotides of a constitutively activated acetylcholine receptor, preferably of a constitutively activated muscarinic receptor, more preferably of a constitutively activated type III muscarinic receptor, having even more preferably the sequence in nucleotide SEQ ID NO: 3. Preferably, said vector is selected from the group comprising Lentivirus, such as, for example, HIV vectors with different envelopes: VSV, gammaretroviral (MLV-A, RD114, GALV), Ross River Virus, Rabies, Measles and Adeno-Associated-Vectors (AAV). Preferably, the sequence in nucleotides of said constitutively activated acetylcholine receptor is under the control of a beta cell specific pig insulin promoter, such as, for example, insulin promoter having the sequence SEQ ID NO: 11.

In one embodiment, the vector comprises the sequence in nucleotides of a constitutively activated type III muscarinic receptor under the control of porcine insulin promoter, with an HA tag and a poly-A sequence fused to its sequence, and comprises the sequence SEQ ID NO: 22.

Another object of the invention is a vector comprising the sequence in nucleotides of GLP-1, preferably containing the A8S mutation and/or an additional sequence allowing the secretion of the encoded polypeptide, having even more preferably the sequence in nucleotide SEQ ID NO: 9. Preferably, said vector is selected from the group comprising Lentivirus, such as, for example, HIV vectors with different envelopes: VSV, gammaretroviral (MLV-A, RD114, GALV), Ross River Virus, Rabies, Measles and Adeno-Associated-Vectors (AAV). Preferably, the sequence in nucleotides of said GLP-1 is under the control of a beta cell specific pig insulin promoter, such as, for example, insulin promoter. In one embodiment, said insulin promoter is specific of beta pig islet cells, leading to an expression of the transgene in beta cells only. An example of nucleic acid sequence of insulin promoter includes, but is not limited to, SEQ ID NO: 11.

In one embodiment, the vector comprises the sequence in nucleotides of GLP1 comprising both the A8S mutation and the Ig K-chain secretion signal, under the control of porcine insulin promoter and with a poly-A sequence fused to its sequence and has the sequence SEQ ID NO: 23.

In one embodiment, the transgenic pig islets or the transgenic pig beta cells of the invention are isolated from adult pig, having at least 6 months, preferably 8 months, more preferably 18 months and even more preferably 2 years. Transgenic pig islets may be used for grafting patients without time delay, but are functional for a limited period of time (for example, when encapsulated in an alginate patch, pig islets isolated from adult pigs may generally be functional in vivo for a period of time of about 4-6 months, preferably about 8 months).

In another embodiment, the transgenic pig islets or the transgenic pig beta cells of the invention are isolated from neonate pig, aged of about 3-4 weeks. These pig islets have to be cultured for about 1 week in order to mature, but are functional for an increased period of time as compared to pig islets isolated from adult pigs.

In one embodiment, the transgenic pig islets isolated from neonate pigs are functional in vivo for a period of time of at least 6 months, preferably of at least 8 months, more preferably of at least 12 months or more.

As used herein, a mature pig islets corresponds to a pig islets (i) comprising differentiated cells, in particular differentiated alpha and beta cells, and (ii) capable of secreting insulin when stimulated with glucose (as may be measured in the conditions of Test D).

Culture conditions that may be applied for maturing transgenic pig islets isolated from neonate pigs are well known from the skilled artisan. A non-limiting example of culture medium that may be used is the following: HAM F10 medium supplemented with 0.25% BSA, 10 mM IBMX, 100 U/mL penicillin-streptomycin, 10 mM glucose, 2 mM glutamine and 10 mM nicotinamide.

Methods for the isolation of pig islets from transgenic pigs are well known to the one skilled in the art. In one embodiment, the isolation of transgenic pig islets is carried out according to the protocol described in Dufrane et al., Xenotransplantation, 2006 and Dufrane et al., Transplantation, 2006, which is briefly summarized below.

According to one embodiment, the isolation protocol comprises a step of exsanguination of pigs, in order to reduce the pancreatic blood content. Briefly, after cerebral death, animals are kept with the heart beating until the time of evisceration. Blood exsanguination is performed by incision of the carotid artery and jugular vein, and the animals are suspended for 1 to 10 minutes, preferably for 4 to 7 minutes by the back legs.

Briefly, pancreases are dissected ex vivo. According to one embodiment, the dissection of pancreases is performed with a warm ischaemia ranging from 5 to 25 minutes. The pancreatic duct is then evidenced and cannulated with an 18-gauge catheter. The gland is then distended with cold storage solution by means of a perfusion solution. According to an embodiment, 1 mL of perfusion solution is used per gram of tissue. Pancreases are stored submerged in preservation solutions. According to one embodiment, the preservation solution is classic University Wisconsin (UW, n=6) or modified-UW (UW-M; no hydroxyethyl starch and low $K^+$/high $NA^+$).

Extracted pancreases are then digested. According to a preferred embodiment, pancreas dissociation is performed with Liberase DL Research Grade (Dispase Low) enzyme, preferably provided by Roche/Boehringer Mannheim. The enzyme is dissolved at cold temperature, preferably at a temperature ranging from about 4 to about 12° C., preferably at about 8° C., in UW-M solution at a concentration ranging from about 0.1 to about 1 mg/mL, preferably at a concentration of about 0.5 mg/mL.

According to one embodiment, the pancreases are digested using the dynamic method, as described by Ricordi et al. (1986, Diabetes, 35: 649-653). Briefly, pig pancreases distended with the enzyme are sliced, loaded on a Ricordi chamber (preferably made of 316 1 stainless steel with seven glass marbles) and digested at 37° C. with a heating circuit, and the chamber is agitated manually. When a significant number of isolated islets appeared in the samples, the digestion circuit is cooled, preferably by addition of cold Ham-F10 medium containing 10% NCS in order to reduce enzyme activity. Cold medium may then be perfused for about 25 to about 40 min. Islets, cells and debris are collected in 250 mL tubes and centrifuged at 4° C. (630 g for 3 min). All cellular pellets are pooled and suspended in 200 mL Ham-F10 medium.

According to another embodiment, the pancreases are digested using the static method, as described by O'Neil et al., 2001. Briefly, the pancreas is infused with a two to four fold volume (mL/g) of liberase PI. The pancreas is injected in order to achieve an adequate distension, placed in a sterile 1 L Nalgene jar and digested by static incubation at 37° C. for 45 to 60 minutes. Digestion is terminated by the addition of Ham-F10+20% NCS based on the visual inspection of the gland. The cell suspension is filtered through a stainless steel mesh with a pore size of 1000 μm and diluted in Ham-F10+ 20% NCS. Digested tissue is then passed over a bed of 6 mm glass beads and through a stainless-steel mesh screen. The tissue effluent is collected with 3 to 4 L of cold Ham-F10+ 10% NCS in 250 mL conical tubes and centrifuged at 700 rpm at 4° C. Islets, cells and debris are collected in 250 mL tubes and centrifuged at 4° C. (630 g for 3 min). All cellular pellets are pooled and suspended in 200 mL Ham-F10 medium.

According to one embodiment, following their isolation, the transgenic pig islets are purified. According to one embodiment, the purification of the transgenic pig islets is carried out using a discontinuous Ficoll gradient as described in Dufrane et al., Xenotransplantation, 2006. Briefly, isolated islets are purified at 4° C. using a discontinuous Ficoll gradient, preferably a Ficoll Euro-Collins gradient. The post-digestion cellular pellet, suspended in 75 mL of Ficoll Euro-Collins solution (density=1.1 g/cm$^3$) is placed in a flat-bottomed tube. Lower gradients of Ficoll are then added sequentially (50 mL of 1.096 g/cm$^3$, 50 mL of 1.060 g/cm$^3$ and 20 mL of Ham-F10 medium). Ham-F10 medium is F-10 nutrient mixture medium, and is commercially available, for example it is provided by N.V. Invitrogen, Belgium. After centrifugation of the gradient tubes at 856 g for 17 minutes, islets are collected from 1.1/1.096 and 1.096/1.060 interfaces. Islets from each interface are suspended in two tubes containing 50 mL Ham-F10+10% NCS serum (NCS stands for newborn calf serum, and is commercially available, for example it is provided by Biochrom AG, Germany). The tubes are centrifuged at 280 g for 3 minutes, the supernatant is removed, and the cells are washed with 150 mL Ham-F10 medium. This procedure may be repeated, such as, for example, three times and, finally, the islets are suspended in 200 mL Ham-F10 medium.

Another object of the invention is a device comprising the transgenic pig islet or the transgenic beta cell of the invention. Preferably, the device of the invention comprises transgenic pig islets as hereinabove described.

According to one embodiment, the device of the invention is an implantable or transplantable device. According to another embodiment, the device of the invention is an injectable device.

According to one embodiment, the device of the invention is biodurable, which means that it shows an improved biostability when implanted or injected to a subject. This improved biostability enables the cells present in the device to remain within a living body for a longer period than is currently the case, which will result in improved treatment efficacy.

In one embodiment of the invention, the device may be a vascularized subcutaneous collagen tube, as described in WO02/32437, in order to allow the development of a prevascularized autologous collagen reservoir for the placement of the transgenic pig islet or of the transgenic pig beta cells. In brief, a closed ended tube of stainless steel mesh containing a loosely fitting Teflon rod is inserted subcutaneously in the intended graft recipient. Six weeks later the rod is removed, leaving a highly vascularized tube of collagen. In one embodiment, the transgenic pig islets or the transgenic beta cells of the invention are inserted into the vascular tube which is then sealed with a Teflon stopper.

In another embodiment of the invention, the device may be a matrix preparation including preparation of gelatin, collagen, and natural carbohydrate polymers.

In another embodiment of the invention, the device may be a plasma thrombin clot—autologous plasma clots produced with allogeneic thrombin.

In another embodiment of the invention, the device may be a suitable biocompatible material such as a capsule to provide additional immune protection of the transplanted transgenic pig islets or beta cells. Encapsulation systems are well-known in the art. Advantageously, the capsule is made of a semi-permeable membrane, which is permeable to glucose, nutrients and insulin, but not to humoral/cellular immune components.

In one embodiment, the semi-permeable membrane is made of a material selected from the group comprising alginate, nitrocellulose, acrylonitrile, agarose and polytetrafluoroethylene. In a preferred embodiment, the semi-permeable membrane is made of alginate.

In another embodiment, the device may be an encapsulation system for living cells, as described in WO2007/046719. According to this embodiment, the encapsulation system comprises a biodurable composition comprising alginate which is rich in mannuronic acid specifically containing between about 50% to 95% mannuronic acid residues, and a polycation having a polydispersity index of <1.5, such as poly-L-ornithine. The encapsulation system may be a biocompatible microcapsule prepared using the composition hereinabove described, and comprising a core layer of high mannuronic acid alginate cross-linked with a cationic cross-linking agent, an intermediate layer of polycations having a polydispersity index of less than about 1.5 forming a semi-permeable membrane, and an outer layer of high mannuronic acid alginate, the microcapsules comprising living cells within the core layer.

In another embodiment, the device may be a microcapsule as described in WO02/032437: sodium alginate used for this procedure is extracted from raw material sources (seaweed) and prepared in a powdered ultrapure form. The encapsulation procedure involves extruding a mixture of transgenic pig islets or beta cells and sodium alginate solution (1.6%) through a droplet generating needle into a bath of gelling cations (calcium chloride). The islets or beta cells entrapped in the calcium-alginate gel are then coated with positively charged poly-L-ornithine followed by an outer coat of alginate (0.05%). The central core of alginate is then liquefied by the addition of sodium citrate. Preferably, most capsules contain 3 transgenic pig islets and have a diameter of 300 to 400 µm.

In another embodiment, the device may be a macrocapsule as described in WO2010/032242. WO2010/032242 discloses a system for transplanting and immunoisolating cells (e.g., functional cells, typically, islets of Langerhans) by an artificial membrane provided by macroencapsulation of the cells in a hydrogel such as an alginate matrix. The hydrogel macroencapsulating the islets is formed so as to have a planar, geometric configuration, e.g., a slab, a sheet, or a disc. Typically, the alginate structure has at least one substantially flat surface. The alginate comprises an ultrapure grade alginate and a defined composition that is cross-linked so as to encapsulate the cells or tissue segments in a hydrogel. Typically, the alginate slab houses transgenic pig islets at a density of 2,000-8,000 islets/cm$^2$. The alginate macroencapsulating the islets typically has a concentration of guluronic acid of less than 50% such that the slab is flexible enough to conform to the shape of the kidney and fit within the subcapsular space thereof, but strong enough to maintain its overall physical characteristics. Additionally, the alginate comprises a dry matter content that is greater than 1.5% such that the slab is strong and stable enough to withstand forces. Typically, the macroencapsulated islets slab provides a ratio of volume of islets to volume of alginate of at least 1:10 (i.e., 10% islets by volume). For some applications, the alginate used to encapsulate the islets is supplemented with collagen. In some applications, the islets are disposed in the center of a primary alginate slab, and a supplementary alginate layer surrounds the encapsulated islets within the primary alginate slab. In such an application, a layer of medical grade collagen may be used in combination with the supplementary alginate layer.

In another embodiment of the invention, the device may be a cellular device as described in WO2007/144389, said device comprising (a) a collagen matrix having a first side and a second side; (b) a first cell layer absorbed onto the first side of the collagen matrix; and (c) a first gelled alginate layer and a second gelled alginate layer; wherein the first gelled alginate layer completely covers the first side of the collagen matrix and the first cell layer; and wherein the second gelled alginate layer completely covers the second side of the collagen matrix.

According to an embodiment, freshly isolated trasnsgenic pig islets or beta cells are encapsulated in an SLM 100 alginate matrix (FMC BioPolymer, Norway) with the Inotech Encapsulation AG Device (Dottikon, Switzerland).

Preferably, the device of the invention is sterilized before implantation or injection into a patient body. Advantageously, the sterilization comprises γ-irradiation, E-beam, ethylene oxide, autoclaving or contacting the device with alcohol prior to addition of the liquid component or contacting with NOx gases, hydrogen gas plasma sterilization.

Preferably, the device possesses a low content of endotoxins. In some embodiments, the cellular device possesses an endotoxin level of less than 100 endotoxin units (EU)/g, less than 90 EU/g, less than 80 EU/g, less than 70 EU/g, less than 60 EU/g, less than 50 EU/g, less than 40 EU/g, less than 30 EU/g, less than 20 EU/g, less than 10 EU/g, less than 5 EU/g, or less than 1 EU/g.

In another embodiment of the invention, the device may be an encapsulation chamber as described in WO02/060409, said device comprising cells, such as, for example transgenic pig islet or beta cells, producing a biologically active substance, such as, for example, insulin, and comprising at least one semi-permeable membrane. The semi-permeable membrane of said device may comprise a biocompatible porous polycarbonate film, wherein the porous polycarbonate film is modified on surface by the creation of polar sites, and wherein the porous polycarbonate film is coated by at least one hydrophilic polymer, such as, for example, cellulose, polyacrylamide, polyvinylpyrrolidone, copolymer of vinyl acetate, polyethylene glycol, hydrophilic poly(meth)acrylate, polyoside and chitosan.

The present invention also relates to a composition comprising the transgenic pig beta cell, the transgenic pig islet or the device of the invention.

The present invention also relates to a pharmaceutical composition comprising the transgenic pig beta cell, the transgenic pig islet or the device of the invention and at least one pharmaceutically acceptable excipient. As used herein, a "pharmaceutically acceptable excipient" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety and purity standards as required by regulatory offices, such as, for example, FDA Office or EMA.

The present invention also relates to a medicament comprising the transgenic pig beta cell, the transgenic pig islet or the device of the invention.

Another object of the invention relates to the use of a transgenic pig islet, a transgenic beta cell, a device, or a composition, pharmaceutical composition or medicament of the invention for treating, or for use in treating, a disease, disorder or condition associated with a deficiency in or absence of endocrine pancreas of beta cells function. Examples of such diseases include, but are not limited to, type I diabetes, type II diabetes, gestational diabetes, latent autoimmune diabetes, type 1.5 diabetes, lipoatrophic diabetes, maturity onset diabetes of the young, neonatal diabetes (e.g. permanent neonatal diabetes or transient neonatal diabetes), prediabetes, steroid-induced diabetes, pancreatic cancer, in particular endocrine pancreas cancer, such as, for example, endocrine pancreatic tumors and pancreatic neuroendocrine carcinomas.

In one embodiment, said disease, disorder or condition is diabetes, such as, for example, type I diabetes, type II diabetes, gestational diabetes, latent autoimmune diabetes, type 1.5 diabetes, lipoatrophic diabetes, maturity onset diabetes of the young, neonatal diabetes (e.g. permanent neonatal diabetes or transient neonatal diabetes), prediabetes, steroid-induced diabetes.

Another object of the invention is a transgenic pig islet, a transgenic beta cell, a device, or a composition, pharmaceutical composition or medicament of the invention for regulating blood glucose levels in a subject in need thereof. In one embodiment, regulating blood glucose levels means restoring a normal fasting blood glucose level, wherein a normal fasting blood glucose levels preferably corresponds to the fasting blood glucose level measured in a normal, i.e. non-diabetic individual of similar age and weight. In one embodiment, the normal fasting blood glucose level is under 110 mg/dL (i.e. 6.1 mmol/L), preferably under 100 mg/dL (i.e. 5.6 mmol/L).

Another object of the invention is a transgenic pig islet, a transgenic beta cell, a device, or a composition, pharmaceutical composition or medicament of the invention for restoring normal insulin secretion levels in subjects in need thereof. In one embodiment, the normal insulin secretion level corresponds to the insulin secretion level induced by a given uptake of glucose in a normal, non-diabetic individual of similar age and weight. In one embodiment, insulin secretion in response to glucose uptake may be measured by glucose tolerance tests (such as, for example, oral glucose tolerance test (OGTT) or intravenous glucose tolerance test (IVGTT)). In one embodiment, in IVGTT in a non-diabetic subject, after administration of an amount of glucose of 0.3-0.5 g/kg, the insulin secretion may reach a maximal value of 100 µU/mL and then decreases to the basal value (15-20 µU/mL).

The present invention also relates to a method for treating, a disease, disorder or condition associated with a deficiency in or absence of endocrine pancreas of beta cells function, comprising or consisting of administering a therapeutically effective amount of a transgenic pig islet, a transgenic pig beta cell, a device, or a composition, pharmaceutical composition or medicament of the invention to a subject in need thereof. Examples of such diseases include, but are not limited to, type I diabetes, type II diabetes, gestational diabetes, latent autoimmune diabetes, type 1.5 diabetes, lipoatrophic diabetes, maturity onset diabetes of the young, neonatal diabetes (e.g. permanent neonatal diabetes or transient neonatal diabetes), prediabetes, steroid-induced diabetes, pancreatic cancer, in particular endocrine pancreas cancer, such as, for example, endocrine pancreatic tumors and pancreatic neuroendocrine carcinomas.

In one embodiment, said disease, disorder or condition is diabetes, such as, for example, type I diabetes, type II diabetes, gestational diabetes, latent autoimmune diabetes, type 1.5 diabetes, lipoatrophic diabetes, maturity onset diabetes of the young, neonatal diabetes (e.g. permanent neonatal diabetes or transient neonatal diabetes), prediabetes, steroid-induced diabetes.

Another object of the invention is a method for regulating blood glucose levels in subjects in need thereof, comprising administering a therapeutically effective amount of a transgenic pig islet, a transgenic beta cell, a device, or a composition, pharmaceutical composition or medicament of the invention to said subject. In one embodiment, regulating blood glucose levels means restoring a normal fasting blood glucose level, wherein a normal fasting blood glucose levels preferably corresponds to the fasting blood glucose level measured in a normal, non-diabetic individual of similar age and weight. In one embodiment, the normal fasting blood glucose level is under 110 mg/dL (i.e. 6.1 mmol/L), preferably under 100 mg/dL (i.e. 5.6 mmol/L).

Another object of the invention is a method for restoring normal insulin secretion levels in a subject in need thereof, comprising administering a therapeutically effective amount of a transgenic pig islet, a transgenic beta cell, a device, or a composition, pharmaceutical composition or medicament of the invention to said subject. In one embodiment, the normal insulin secretion level corresponds to the insulin secretion level induced by a given uptake of glucose in a normal, i.e. non-diabetic individual of similar age and weight. In one embodiment, insulin secretion in response to glucose uptake may be measured by glucose tolerance tests (such as, for example, oral glucose tolerance test (OGTT) or intravenous glucose tolerance test (IVGTT)). In one embodiment, in IVGTT in a non-diabetic subject, after administration of an amount of glucose of 0.3-0.5 g/kg, the insulin secretion may reach a maximal value of 100 µU/mL and then decreases to the basal value (15-20 µU/mL).

Another object of the invention is a method for treating, a disease, disorder or condition associated with a deficiency in or absence of endocrine pancreas of beta cells function, for regulating blood glucose levels or for restoring normal insulin secretion levels in a subject in need thereof, said method comprising administering to said subject a therapeutically effective amount of transgenic pig beta cells or transgenic pig islets wherein the PKA and the PKC pathways are constitutively activated, thereby increasing insulin secretion by said subject.

In one embodiment, said increase in insulin secretion results from the expression by said transgenic cell or islet of a constitutively activated M3 muscarinic receptor, leading to an increased hydrolysis of PIP2, resulting in an increased synthesis of IP3 and DAG, thereby activating the PKC pathway and increasing the excretion of $Ca^{2+}$ within the cytoplasm, thereby enhancing insulin synthesis and secretion.

In one embodiment, said increase in insulin secretion results from the expression by said transgenic cell or islet of GLP-1, thereby activating the adenyl cyclase enzyme, thereby increasing cAMP production, thereby
 (i) activating the enzyme protein kinase A (PKA) thereby activating proteins involved in the insulin secretory process (such as, for example, PDX-1); and
 (ii) inducing conformal changes to G-protein Rap1, thereby potentiating insulin exocytosis by enlarging the size of the pool of granules available for the direct release;
thereby enhancing insulin synthesis and secretion.

In an embodiment, the transgenic pig islet, the transgenic pig beta cell, the device, or a composition, pharmaceutical composition or medicament of the invention is administered through implantation, transplantation or injection. Preferably, the administration is made subcutaneously, intraperitoneally, intramuscularly, in or under the kidney capsules.

According to one embodiment, the number of transgenic pig beta cells or of pig islets administered (i.e. the therapeutically effective amount) ranges from 10000 to 50000 IEQ/kg of body weight, preferably from 30000 to 50000 IEQ/kg of body weight. IEQ means pig islets equivalents.

According to an embodiment, when devices are used, one or more devices may be administered, such as, for example, 1, 2, 3, 4, 5, 6, 7, 8, 9, 10 or more.

In one embodiment, the subject in need thereof further receives an immunosuppressive treatment. In one embodiment, the administration of transgenic pig islet, transgenic pig beta cell, device, or a composition, pharmaceutical composition or medicament and of the immunosuppressive treatment may be simultaneous or sequential. Advantageously, the immunosuppressive treatment comprises or consists of the administration of at least one product selected from the group comprising daclizumab, tacrolimus, rapamycin, mycophenolate mofetil, cyclosporine, deoxyspergualin or deoxyspergualin analogue, soluble complement receptor 1, anti-CD154 antibody, ATG, methylprednisolone, anti-IL-2R antibody, basiliximab, FTY720, everolimus, leflunomide, sirolimus, belatacept, CTLA4-Ig, cobra venom.

Preferably, when modified pig islets are administered without device, an immunosuppressive treatment is carried out.

Preferably, the subject is a mammal, preferably a primate, including human and non-human primates, more preferably a human. In one embodiment, the subject is a male. In another embodiment, the subject is a female. In another embodiment, a subject may also refer to a pet, such as, for example, a dog, a cat, a guinea pig, a hamster, a rat, a mouse, a ferret, a rabbit and the like.

According to an embodiment, the subject is affected by a disease, disorder or condition associated with a deficiency in or absence of endocrine pancreas or beta cells function. Preferably, the subject is affected by Type I Diabetes Mellitus or Type II Diabetes Mellitus.

EXAMPLES

The present invention is further illustrated by the following examples.

Example 1

Isolated pig islets were cultured overnight at 37° C., 5% $CO_2$/95% $O_2$ in RMPI medium containing 10% heat-inactivated FCS, 100 IU/ml penicillin, 100 µg/ml streptomycin, 5 mmol/l glucose. Then, isolated pig islets were incubated for 2 hours in 1 mL of Krebs-Ringer buffer at 1 mmol/L or 15 mmol/L glucose, optionally supplemented with 20 nM phorbol myristate acetate (PMA, a direct activator of the PKC pathway) and/or 1 µM forskolin (an indirect activator of the PKA pathway). Finally, insulin was quantified in recovered media and in incubated islets by radioimmuno-assay.

Figure 1:
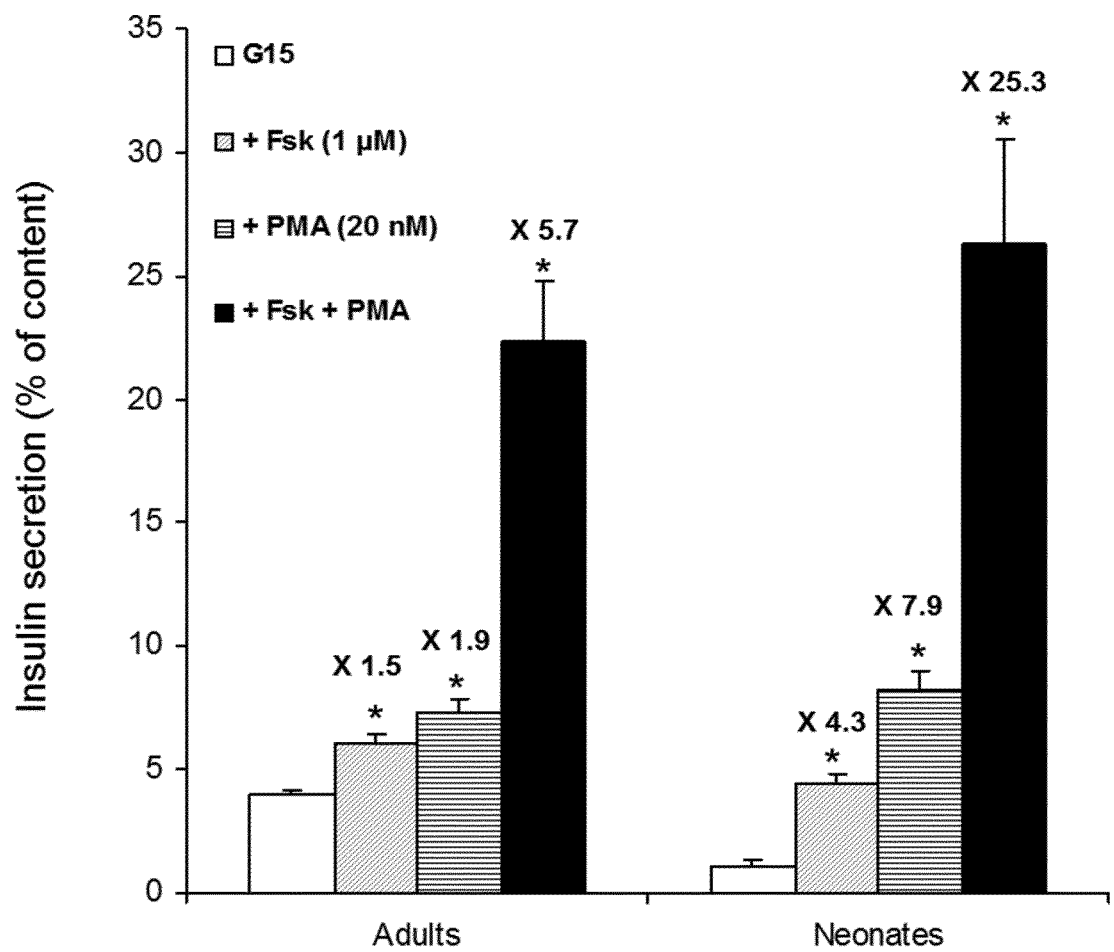
FIG. 1 is a histogram showing the insulin secretion from adult and neonate isolated pig islets. Batches of 200 islets were incubated in 1 ml krebs medium containing 15 mM glucose (G15) alone or in combination with forskolin (Fsk; 1 µM), phorbol myristate acetate (PMA; 20 nM) or both Fsk and PMA. Insulin secretion was measured in the incubation media and expressed as a percentage of total insulin content of each batch of islets. The numbers above the columns represent the fold increase of insulin secretion in test groups compared to 15 mM glucose alone. * p<0.05. Values are means±SEM for n=5-21 from 8 different adult preparations and n=11-43 from 11 different neonate preparations.

As shown in FIG. 1, direct PKC activation by PMA increases glucose-induced insulin secretion by 2-fold in isolated pig islets isolated from adult pigs and up to 8-fold in pig islets isolated from neonate pigs, thus improving porcine islet responsiveness to glucose. We also observed slightly smaller increases when beta-cell cAMP was elevated by forskolin to activate PKA and Epac2. Interestingly, when we exposed the transgenic pig islets to both PMA and forskolin in the presence of 15 mM glucose, we observed an unexpected synergy in the secretory response which was then augmented by almost 6-fold in adult islets and 25-fold in neonate islets. These results thus demonstrate an unexpected synergistic effect of PKC activation and PKA activation on insulin secretion.

Example 2

In order to verify the expression of transgenic proteins, the activation of the targeted pathways and the effects of such activation on glucose-induced insulin secretion, a line of murine beta-cells (MIN6) was transfected.

The expression of transgenic proteins was verified at the mRNA level by RT-PCR. The sequence of the activated muscarinic receptor differs greatly from the wild type receptor and expression of the protein can thus be validated by western blotting of transfected MIN6 cells extracts using an antibody specific to a tag that has been added to the receptor sequence. GLP-1 production was verified by measuring the amount of intracellular GLP-1 in transgenic and control cells as well as measuring GLP-1 secretion in culture media.

To verify the effect of the transgenic proteins on insulin secretion, transfected and control MIN6 cells were challenged by an increase of glucose concentration during static incubation experiments. Insulin secretion was measured and the stimulation index i.e., the ratio between insulin secretion at high glucose and insulin secretion at low glucose, of transgenic and control cells was calculated. In brief, $2 \cdot 10^5$ cells were seeded in 12-well plates and cultivated for 48 h before they were transfected with one the plasmids carrying the GLP-1 (7-37) gene (GLP-1), the mutated GLP-1 (7-A8S-37) gene (GLP-1 Ser8) or the constitutively activated muscarinic receptor gene (M3). Control cells were simply exposed to Lipofectamine without any plasmidic DNA. 48 h after transfection, cells were starved then incubated for 2 h in a 1 mL Krebs-Ringer buffer containing either 1 or 15 mM glucose. Insulin secretion was measured in the incubation media and expressed as a percentage of total insulin content of the cells.

Figure 2:
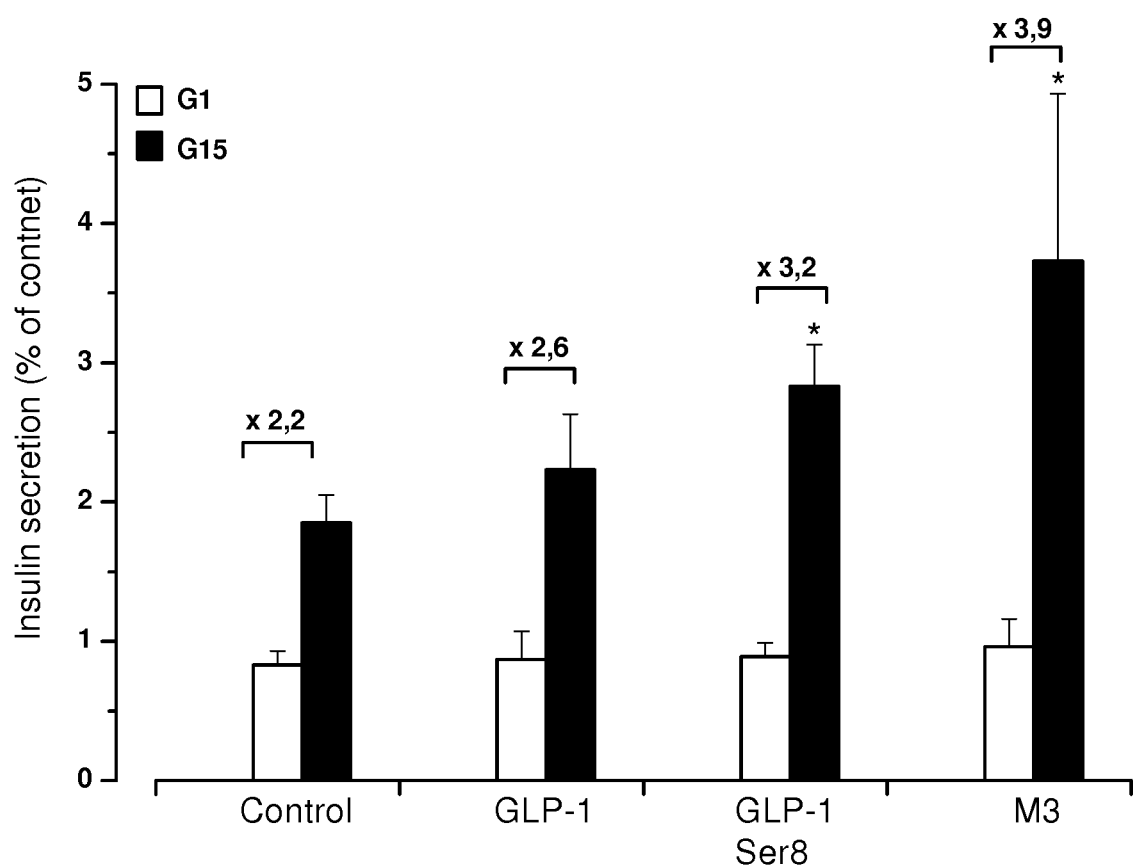
FIG. 2 is a histogram showing glucose-induced insulin secretion from transfected Min6 cells incubated with 1 (G1) or 15 mM (G15) glucose. The numbers above pairs of columns represent the stimulation ratio (G15/G1) in each group. * p<0.05 indicates significant difference between test groups and controls. Values are means±SEM for n=15-21 from 7 different experiments.

FIG. 2 shows that transgenic expression of GLP-1 in Min6 cells causes a slight non-significant increase of glucose-induced insulin secretion (stimulation index 2.6 vs 2.2 in control cells). Interestingly, the transgene encoding a modified GLP-1 (GLP-1 Ser8) with a larger half-life induced a greater significant increase of the secretory response to 15 mM glucose (stimulation index 3.2 vs 2.2 in control cells). Expression of a constitutively activated type-3 muscarinic receptor (M3) in Min6 cells significantly increased insulin secretion induced by 15 mM glucose (stimulation index 3.9 vs 2.2 in controls).

These results thus show that the used plasmids successfully induce expression of the molecules of interest and that this expression increases the secretory response to glucose.

Example 3

The effect of transgenic activation of PKA and PKC pathways was evaluated in isolated pig islets. For this purpose, the GLP-1 Ser8 and M3R sequences were inserted in a pENTCMV adenoviral vector to permit expression of transgenic GLP-1 (GLP-1 Ser8) and activated muscarinic receptor (M3R) in primary islet cells. For co-expression of GLP-1 and M3R, the two sequences were inserted in the same bicistronic vector to study the effect of concomitant activation of PKA and PKC on pig islet insulin secretion. Neonatal pig islets cultivated in HAM F10 (panel A) and adult pig islets cultivated in RPMI (panel B) were exposed to GLP-1, M3R or GLP-1+M3R viral expression vectors at a multiplicity of infection of 200 (MOI=200) during 48 hours before glucose challenge. Islets were then incubated for 2 hours in 1 mL of Krebs-Ringer buffer containing 1 mM or 15 mM glucose. Insulin was then quantified in recovered media and in incubated islets by radioimmunoassay.

Figure 3:
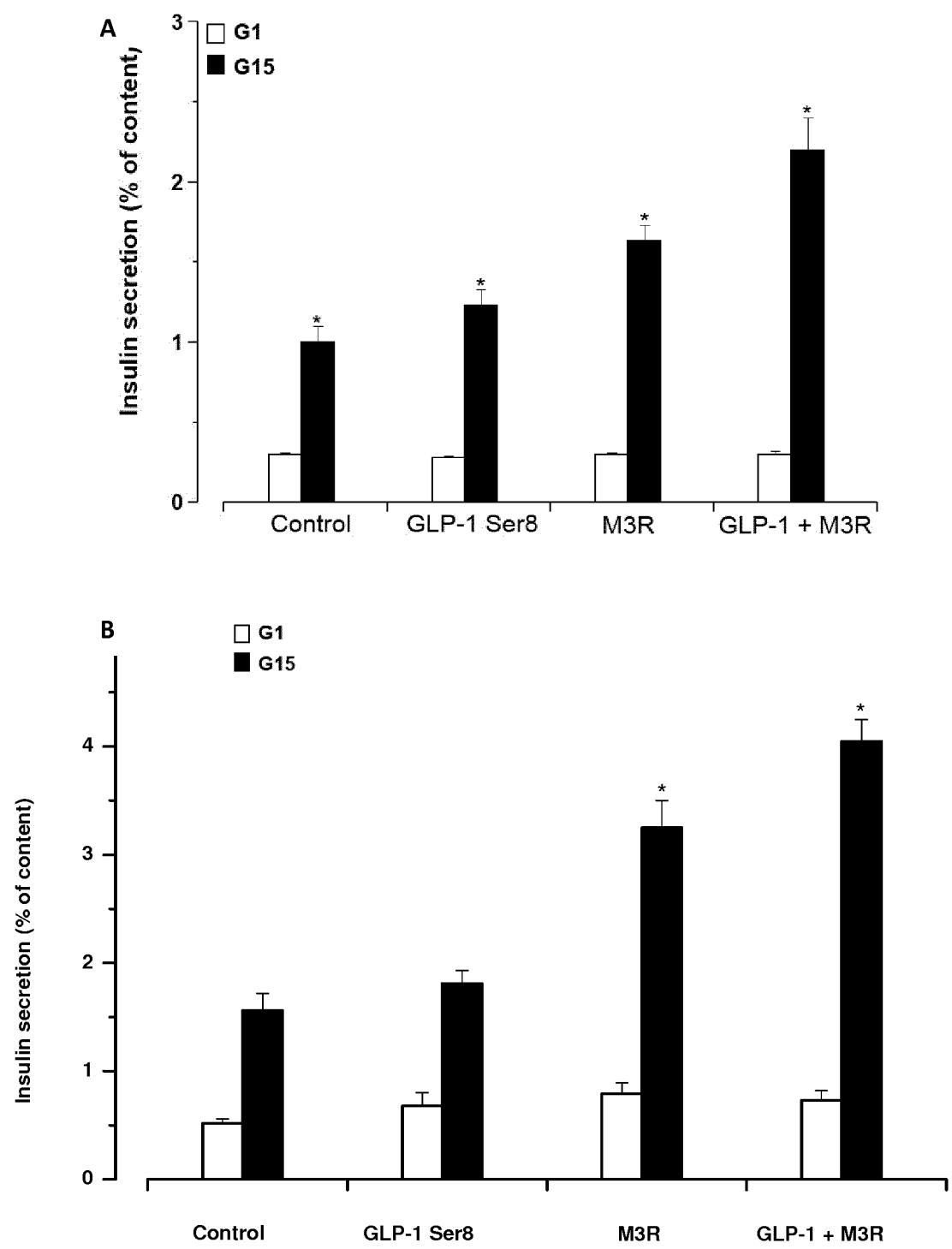
FIG. 3 is a combination of two histograms showing the insulin secretion from neonatal (A) and adult (B) isolated pig islets exposed to 200 MOI viral expression vectors carrying sequences coding for GLP-1 (GLP-1 Ser8), activated muscarinic receptor (M3R) or both (GLP-1+M3R) during 48 hours. Batches of 200 islets were incubated in 1 ml krebs medium containing 1 mM glucose (G1) or 15 mM glucose (G15). Insulin secretion was measured in the incubation media and expressed as a percentage of total insulin content of each batch of islets. * p<0.05. Values are means ±SEM for n=38-46 from 10 different preparations.

As shown in FIG. 3, stimulation index in control islets was at 3.3 for neonatal pig islets and 3 for adults. Islets expressing GLP-1 Serb showed improved, however non-significantly different from controls insulin secretion with a stimulation index of 4.4 in neonates but there was no effect on secretion in adults (stimulation index: 2.7). Insulin secretion was further increased and the difference compared to controls was significant when islets were infected with M3R expression vector resulting in a stimulation index of 5.4 and 4.1 in neonates and adults respectively. Finally, and as expected from the results shown in example 1, neonatal islets co-expressing GLP-1 and M3R showed a synergetic response in terms of insulin secretion since their stimulation index was 7.3. This effect was also observed although to a less degree in adult islets (stimulation index: 5.5).

Figure 4:
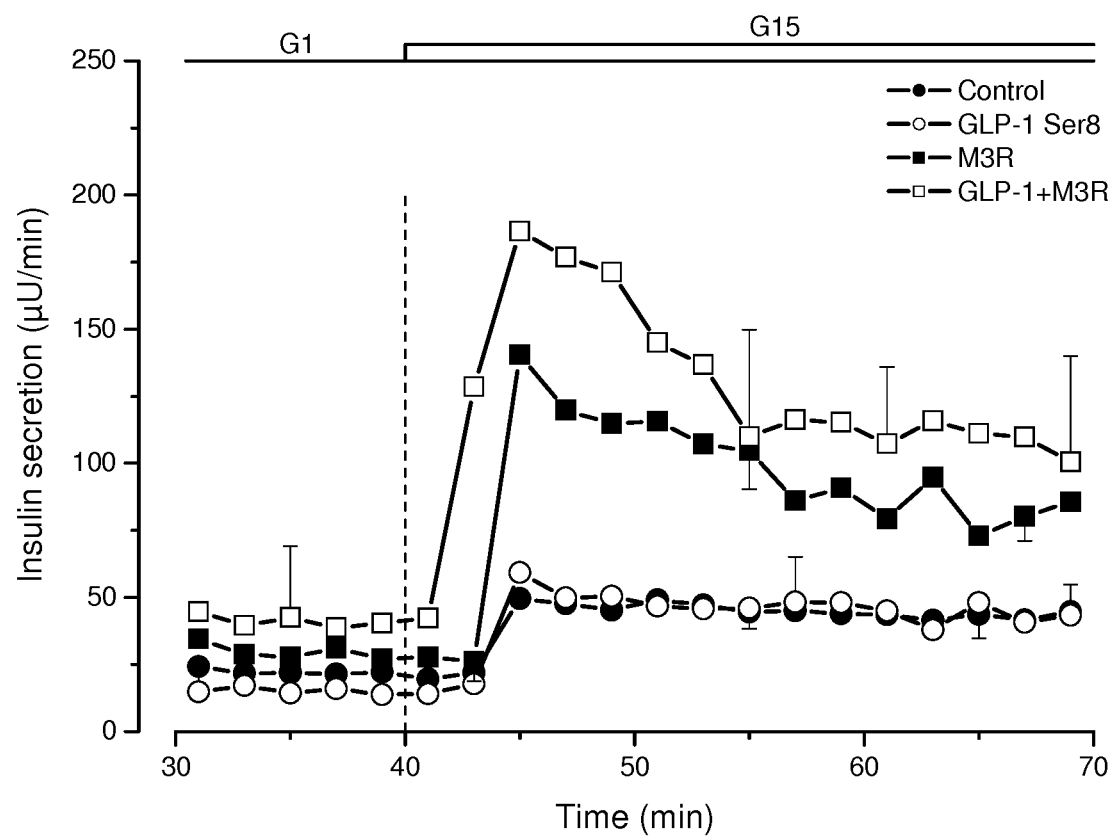
FIG. 4 is a graph showing the insulin secretion of isolated adult pig islets exposed to 200 MOI viral expression vectors carrying sequences coding for GLP-1 (GLP-1 Ser8), activated muscarinic receptor (M3R) or both (GLP-1+M3R) during 48 hours. Batches of 600 islets were perifused in krebs medium containing 1 mM glucose (G1) then 15 mM glucose (G15) as indicated on top of the figure. Insulin secretion was then measured in the effluent fractions. Values are means±SEM for n=3-4 from 4 different preparations.

The effect of transgenic PKA and PKC activation on glucose-induced insulin secretion was also tested during dynamic islet perifusion experiments. Control and virus-treated adult islets were placed in perifusion chambers sealed with 0.2 µm filters. Islets were first perifused with 1 mM glucose (G1) krebs medium during 30 minutes for equilibrium then during 10 minutes in G1 with media collection every 2 minutes followed by 30 minutes stimulation with G15. As shown in FIG. 4 and in agreement with what we observed in static incubations, GLP-1 expression had virtually no effect on acute insulin secretion. M3R expression increased both phases of glucose-induced insulin secretion but this increase was greater when adult pig islets co-expressed GLP-1 and M3R.

These results thus confirm data obtained using pharmacological activation of PKA and PKC pathways in pig islet cells. Our conclusion is that concomitant activation of both pathways in pig beta-cells would be the best strategy to obtain functionally-enhanced pig islets.

The invention claimed is:

1. An isolated transgenic pig beta cell, which comprises and expresses the constitutively active type III muscarinic receptor having the amino acid sequence of SEQ ID NO: 4 and the GLP-1 having the amino acid sequence of SEQ ID NO: 6 or SEQ ID NO: 20, wherein the PKC and the PKA pathway are constitutively activated in said isolated transgenic pig beta cell.

2. The isolated transgenic pig beta cell according to claim 1, wherein the cell expresses GLP-1 having the amino acid sequence SEQ ID NO: 6.

3. An isolated transgenic pig islet comprising the transgenic pig beta cell according to claim 1.

4. An ex vivo method for obtaining the isolated transgenic pig beta cell according to claim 1 or an isolated transgenic pig islet comprising the isolated transgenic pig beta cell according to claim 1, wherein said method comprises administering to the isolated transgenic pig beta cell an expression vector comprising a nucleic acid sequence encoding the constitutively active type III muscarinic receptor having the amino acid sequence of SEQ ID NO: 4 and an expression vector comprising the nucleic acid sequence encoding the GLP-1 having the amino acid sequence of SEQ ID NO: 6 or SEQ ID NO: 20.

5. A transgenic pig comprising the isolated transgenic pig beta cell according to claim 1.

6. A device comprising the isolated transgenic pig beta cell according to claim 1 or an isolated transgenic pig islet comprising the transgenic pig beta cell according to claim 1.

7. The device according to claim 6, wherein said isolated transgenic pig beta cell or said isolated transgenic pig islet are encapsulated in an alginate composition.

8. The isolated transgenic pig beta cell according to claim 1, wherein said GLP-1 is operably linked to an additional sequence allowing for its secretion and wherein said additional sequence is the Ig K-chain signal peptide having the amino acid sequence of SEQ ID NO: 8.

9. The method according to claim 8, wherein said disease, disorder or condition related to the impaired function of endocrine pancreas or beta cell is selected from the group comprising type I diabetes, type II diabetes, gestational diabetes, latent autoimmune diabetes, type 1.5 diabetes, lipoatrophic diabetes, maturity onset diabetes of the young, neonatal diabetes, prediabetes, steroid-induced diabetes, and pancreatic cancer.

10. The method according to claim 8, wherein said disease, disorder or condition related to the impaired function of endocrine pancreas or beta cell is permanent neonatal diabetes or transient neonatal diabetes.

11. The method according to claim 8, wherein said disease, disorder or condition related to the impaired function of endocrine pancreas or beta cell is an endocrine pancreas cancer.

12. The method according to claim 8, wherein said disease, disorder or condition related to the impaired function of endocrine pancreas or beta cell is an endocrine pancreatic tumor or a pancreatic neuroendocrine carcinoma.

13. The isolated transgenic pig beta cell according to claim 1, wherein said GLP-1 has an additional sequence allowing for its secretion.

14. The isolated transgenic pig beta cell according to claim 1, wherein said GLP-1 is operably linked to an additional sequence allowing for its secretion and wherein said additional sequence is the Ig K-chain signal peptide having the amino acid sequence of SEQ ID NO: 8.

15. The isolated transgenic pig beta cell according to claim 1, wherein said GLP-1 has the amino acid sequence of SEQ ID NO:20.

16. The isolated transgenic pig beta cell according to claim 1, wherein said GLP-1 is operably linked to an additional sequence allowing for its secretion and has the amino acid sequence of SEQ ID NO: 10.

17. The isolated transgenic pig beta cell according to claim 1, wherein the isolated transgenic pig beta cell is a transgenic neonate pig beta cell.

18. A method for treating a disease, disorder or condition related to the impaired function of endocrine pancreas or beta cell in a subject in need thereof, comprising administering to the subject the device of claim 6.

* * * * *